US006544523B1

(12) United States Patent
Chu

(10) Patent No.: US 6,544,523 B1
(45) Date of Patent: Apr. 8, 2003

(54) MUTANT FORMS OF FAS LIGAND AND USES THEREOF

(75) Inventor: Keting Chu, Burlingame, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/968,686

(22) Filed: Nov. 12, 1997

Related U.S. Application Data

(60) Provisional application No. 60/039,972, filed on Feb. 10, 1997, and provisional application No. 60/030,871, filed on Nov. 13, 1996.

(51) Int. Cl.$^7$ .................... C07H 21/00; C07K 14/435
(52) U.S. Cl. .................. 424/192.1; 424/198.1; 435/69.7; 435/69.8; 435/325; 435/252.3; 435/320.1; 530/350; 536/23.1; 536/23.4; 536/23.5; 514/12
(58) Field of Search ................. 435/69.7, 325, 435/361, 252.3, 320.1, 69.1, 69.8; 536/23.4, 23.1, 23.5; 530/350; 935/10; 424/192.1, 198.1; 514/12

(56) References Cited

U.S. PATENT DOCUMENTS

| | | | |
|---|---|---|---|
| 4,399,216 A | 8/1983 | Axel et al. ................ 435/6 |
| 4,405,712 A | 9/1983 | Waude et al. ............. 435/5 |
| 4,411,648 A | 10/1983 | Davis et al. ............. 604/21 |
| 4,551,433 A | 11/1985 | DeBoer ................. 435/253 |
| 4,560,655 A | 12/1985 | Baker .................. 435/241 |
| 4,603,112 A | 7/1986 | Paoletti et al. .......... 435/235 |
| 4,657,866 A | 4/1987 | Kumar .................. 435/240 |
| 4,745,051 A | 5/1988 | Smith et al. ............ 435/240 |
| 4,762,915 A | 8/1988 | Kung et al. ............. 530/405 |
| 4,767,704 A | 8/1988 | Cleveland et al. ........ 435/68 |
| 4,769,330 A | 9/1988 | Paoletti et al. ......... 435/172.3 |
| 4,777,127 A | 10/1988 | Suni et al. .............. 435/5 |
| 4,797,368 A | 1/1989 | Carter et al. ........... 435/235 |
| 4,837,148 A | 6/1989 | Cregg ................ 435/172.3 |
| 4,853,230 A | 8/1989 | Lovgren et al. .......... 424/466 |
| 4,859,609 A * | 8/1989 | Dull et al. .............. 436/501 |
| 4,861,719 A | 8/1989 | Miller .................. 435/236 |
| 4,927,762 A | 5/1990 | Darfler ................. 435/240.31 |
| 4,928,555 A | 5/1990 | Nuti ..................... 74/745 |
| 4,980,289 A | 12/1990 | Temin et al. ........... 435/235 |
| 5,010,175 A | 4/1991 | Rutter et al. ........... 530/334 |
| 5,091,309 A | 2/1992 | Schlesinger et al. ...... 435/69.1 |
| 5,139,941 A | 8/1992 | Muzyczka .............. 435/172.3 |
| 5,149,655 A | 9/1992 | McCabe et al. .......... 435/287 |
| 5,166,057 A | 11/1992 | Palese et al. ........... 435/69.1 |
| 5,166,320 A | 11/1992 | Wu et al. ................ 530/395 |
| 5,173,414 A | 12/1992 | Lebkowski et al. ........ 435/172.3 |
| 5,194,392 A | 3/1993 | Geysen ................ 436/518 |
| 5,206,152 A | 4/1993 | Sukhatme .............. 435/69.1 |
| 5,217,879 A | 6/1993 | Huang et al. ........... 435/69.1 |
| 5,219,740 A | 6/1993 | Miller et al. ........... 435/69.6 |
| 5,222,936 A | 6/1993 | Stephen et al. .......... 604/20 |
| 5,223,408 A | 6/1993 | Goeddel et al. ......... 435/69.3 |
| 5,252,479 A | 10/1993 | Srivastava ............. 435/235.1 |
| 5,286,254 A | 2/1994 | Shapland et al. ......... 604/21 |
| 5,288,641 A | 2/1994 | Roizman ............... 435/320.1 |
| 5,324,655 A | 6/1994 | Kriegler et al. ......... 435/240.2 |
| 5,354,678 A | 10/1994 | Lebkowski et al. ....... 435/172.3 |
| 5,399,346 A | 3/1995 | Anderson et al. ........ 424/93.21 |
| 5,422,120 A | 6/1995 | Kim .................. 424/450 |
| 5,474,935 A | 12/1995 | Chartejee et al. ....... 435/320.1 |
| 5,478,745 A | 12/1995 | Samulski et al. ........ 435/320.1 |
| 5,580,859 A | 12/1996 | Felgner et al. ......... 514/44 |

FOREIGN PATENT DOCUMENTS

| | | |
|---|---|---|
| EP | 0 675 200 A1 | 10/1995 |
| WO | WO 89/01973 | 3/1989 |
| WO | WO 89/02468 | 3/1989 |
| WO | WO 89/05349 | 6/1989 |
| WO | WO 89/09271 | 10/1989 |
| WO | WO 95/18819 | 7/1995 |
| WO | WO 95/32627 | 12/1995 |
| WO | WO 97/18307 | 5/1997 |
| WO | WO 97/33617 | 9/1997 |

OTHER PUBLICATIONS

Tanaka, et al., Expression of the functional soluble form of human Fas ligand in activated lymphocytes, The EMBO Journal, 14(6):1129–1135 (Mar. 15, 1995).

International Search Report based on PCT/US 97/20864, International Filing Date Nov. 11, 1997.

A.N. Barclay et al., *The Leucocyte Antigen Factsbook*, Academic Press, London, 1993 at pp. 166–167 and 188–189.*

Adachi, et al., *Targeted mutation in the Fas gene causes hyperplasia in peripheral lymphoid organs and liver*, Nature Genetics, 11(3):294–300 (Nov., 1995) (Abstract Only).

Aggarwal, et al., *Fas Antigen Signals Proliferation of Normal Human Diploid Fibroblast and Its Mechanism is Different From Tumor Necrosis Factor Receptor*, FEBS Letter, 364(1):5–8 (May 1, 1995) (Abstract Only).

(List continued on next page.)

*Primary Examiner*—Lorraine Spector
(74) *Attorney, Agent, or Firm*—Donald J. Pochopien; Kimberly L. Morley; Robert P. Blackburn

(57) ABSTRACT

The invention provides for DNA encoding Fas ligand muteins and chimeras and the proteins encoded thereby. The invention further includes the use of DNA and vectors to produce transformed cells expressing the mutant or chimeric Fas ligand. When the Fas ligand of the invention is a non cleavable form, the cells expressing the Fas ligand are useful in vitro for identifying Fas expressing cells and in vitro or in vivo for reducing populations of Fas expressing cells. Thus, in other embodiments, the present invention is also directed to a method for treating a patient, for example a mammal, for autoimmune disease or transplant rejection by administering a Fas ligand therapeutic agent. The therapeutic agent is a polypeptide, a polynucleotide encoding the polypeptide or a small molecule. The polypeptides include full-length Fas ligand polypeptide, or a biologically active variant, derivative, portion, fusion or peptide thereof.

27 Claims, No Drawings

OTHER PUBLICATIONS

Aichele, et al., *Peptide–Induced T–Cell Tolerance to Prevent Autoimmune Diabetes in a Transgenic Mouse Model*, Proceeding of the National Academy of Sciences of the United States of America, 91(2):444–8 (Jan. 18, 1994) (Abstract Only).

Alexander, et al., *Analysis of Effector Mechanisms in Murine Cardiac Allograft Rejection*, Transplant Immunology, 4(1):46–8 (Mar., 1996) (Abstract Only).

Anderson, *Acute Kidney Graft Rejection Morphology and Immunology*, Apmis. Supplementum, 67:1–35 (1997) (Abstract Only).

Anderson, et al., *Insulin–dependent diabetes in the NOD mouse model. II. Beta cell Destruction in Autoimmune Diabetes is a TH2 and not a TH1 Mediated Event*, Autoimmunity, 15(2):113–22 (1993) (Abstract Only).

Aoki, et al., *Clonal expansion but lack of subsequent clonal deletion of bacterial superantigen–reactive T cells in murine retroviral infection*, Journal of Immunology, 153(8):3611–21 (Oct. 15, 1994) (Abstract Only).

Arase, et al., *Fas–Mediated Cytotoxicity by Freshly Isolated Natural Killer Cells*, Journal of Experimental Medicine, 181(3):1235–8 (Mar. 1, 1995) (Abstract Only).

Arnold, et al., *Vaccine Development for Aids through Molecular Surgery of a Human Common Cold Virus Surface*, HIV and AIDS: Pathogenesis, Therapy and Vaccine, L401, UCLA Symposia, (Mar. 31–Apr. 6, 1990) (Abstract Only).

Asahara, et al., *Expression of Fas/Fas Ligand and Proto–Oncogenes in Rheumatoid Synovial Tissues*, Nippon Rinsho, Japanese Journal of Clinical Medicine, 54(7):1960–4 (Jul., 1996) (Abstract Only).

Asahara, et al., *Expression of Fas Antigen and Fas Ligand in the Rheumatoid Synovial Tissue*, Clinical Immunology and Immunopathology, 81(1):27–34 (Oct., 1996).

Badley, et al., *Upregulation of Fas Ligand Expression by Human Immunodeficiency Virus in Human Macrophages Mediates Apoptosis of Uninfected T Lymphocytes*, Journal of Virology, 70(1):199–206 (Jan., 1996) (Abstract Only).

Baker, et al., *Perforin and Fas–Mediated Cytotoxic Pathways are not Required for Allogeneic Resistance to Bone Marrow Grafts in Mice*, Biol Blood Marrow Transplant, 1(2):69–73 (Dec., 1995) (Abstract Only).

Baker, et al., *The role of cell–mediated cytotoxicity in acute GVHD after MHC–matched allogeneic bone marrow transplantation in mice*, Journal of Experimental Medicine, 183(6):2645–56 (Jun. 1, 1996) (Abstract Only).

Bellgrau, et al., *A role for CD95 ligand in preventing graft rejection*, Nature, 377:630–632 (Oct. 19, 1995).

Berke, et al., *PEL's and the Perforin and Granzyme Independent Mechanism of CTL–Mediated Lysis*, Immunological Reviews, 146:21–31 (Aug. 1995) (Abstract Only).

Berke, *Killing Mechanisms of Cytotoxic Lymphocytes*, Curr. Opin Hematol, 4(1):32–40 (Jan., 1997).

Berke, *TheCTL's Kiss of Death*, Cell, 81(1):9–12 (Apr. 7, 1995) (Abstract Only).

Berkner, *Development of Adenovirus Vectors for the Expression of Heterologous Genes*, Biotecniques 6(7):616 (1988).

Boise, et al., *Receptors that regulate T–cell susceptibility to apoptotic cell death*, Annals of the New York Academy of Sciences, 766:70–80 (Sep. 7, 1995) (Abstract Only).

Boldin, et al., *A Novel Protein that Interacts with the Death Domain of Fas/APO1 Contains a Sequence Motif Related to the Death Domain*, Journal of Biological Chemistry, 270(14):7795–8 (Apr. 7, 1995) (Abstract Only).

Bolling, et al., *The Time Course of CTLAIg Effect on Cardiac Allograft Rejection*. Journal of Surgical Research, 63(1):320–323 (Jun., 1996) (Abstract Only).

Bonomo, et al., *Pathogenesis of post–thymectomy autoimmunity. Role of syngeneic MLR–reactive T cells*, 154(12):6602–11 (Jun. 15, 1994) (Abstract Only).

Braun, et al., *Cytotoxic T cells deficient in both functional fas ligand and perforin show residual cytolytic activity yet lose their capacity to induce lethal acute graft–versus–host disease*, Journal of Experimental Medicine, 183(2):657–61 (Feb. 1, 1996) (Abstract Only).

Brossart, et al., *Selective Activation of Fas/Fas Ligand–Mediated Cytotoxicity by a Self Peptide*, Journal of Experimental Medicine, 183(6):2449–58 (Jun. 1, 1996) (Abstract Only).

Burmester, et al., *Management of Early Inflammatory Arthritis. Intervention with Immunomodulatory Agents: Monoclonal Antibody Therapy*, Baillieres Clinical Rheumatology, 6(2):415–34 (Jun. 1992) (Abstract Only).

Bussing, et al., *Induction of Apoptosis in Human Lymphocytes Treated with Viscum Album L. is Mediated by the Mistletoe Lectins*, Cancer Letters, 99(1):59–72 (Jan. 19, 1996 (Abstract Only).

Candinas, et al., *T Cell Independence of Macrophage and Natural Killer Cell Infiltration, Cytokine Production, and Endothelial Activation During Delayed Xenograft Rejection*, Transplantation, 62(12):1920–1927 (Dec. 27, 1996).

Caspi, et al., *Genetic Factors in Susceptibility and Resistance to Experimental Autoimmune Uveoretinitis*, Current Eye Research, 11 Suppl:81–6 (1992) (Abstract Only).

Chandler, et al. *Transplant Rejection Mechanisms and Treatment*, Arch Surg 128:279–283 (Mar., 1993) (Abstract Only).

Chen, et al., *Polyreactive Antigen–Binding B Cells in the Peripheral Circulation are IgD+ and B7–*, European Journal of Immunology, 26(12):2916–2923 (Dec., 1996) (Abstract Only).

Chmura, et al., *Loss of Ceramide Production Confers Resistance to Radiation–Induced Apoptosis*, Cancer Research, 57(7):1270–1275 (Apr. 1, 1997) (Abstract Only).

Chu, et al., *A Fas–Associated Protein Factor, FAF1, Potentiates Fas–Mediated Apoptosis*. Proceedings of the National Academy of Sciences of the United States of America, 92(25):11894–8 (Dec. 5, 1995) (Abstract Only).

Cleary, et al., *Opposing Roles of CD95 (Fas/APO–1) and CD40 in the Death and Rescue of Human Low Density Tonsillar B Cells*, Journal of Immunology, 155(7):3329–37 (Oct. 1, 1995) (Abstract Only).

Clement, et al., *Fas and Tumor Necrosis Factor Receptor–Mediated Cell Death: Similarities and Distinctions*, Journal of Experimental Medicine, 180(2):557–67 (Aug. 1, 1994) (Abstract Only).

Cone, et al., *High–efficiency gene transfer into mammalian cells: Generation of helper–free recombinant retrovirus with broad mammalian host range*, Proc. Natl. Acad. Sci., 81:6349 (1984).

Constantinescu, et al., *Effects of the Angiotensin Converting Enzyme Inhibitor Captopril on Experimental Autoimmune Encephalomyelitis*, Immunopharmacology and Immunotoxicology, 17(3):471–91 (Aug., 1995) (Abstract Only).

Coppel, et al., *Primary biliary cirrhosis: the molecule and the mimic*, Immunological Reviews, 144:17–49 (Apr., 1995) (Abstract Only).

Corcoran, et al., *Feline Asthma Syndrome: a Retrospective Study of the Clinical Presentation in 29 Cats*, Journal of Small Animal Practices, 36(11):481–488 (Nov., 1995).

Cosman, *A Family of Ligands for the TNF Receptor Superfamily*, Stem Cells 12:440–455 (1994) (*Abstract Only*).

Costagliola, et al., *Recombinant Thyrotropin Receptor and the Induction of Autoimmune Thyroid Disease in BALB/c Mice: a New Animal Model*, Endocrinology, 135(5):2150–9 (Nov., 1994) (Abstract Only).

Daniel, et al., *Activation and Activation–induced Death of Human Tonsillar B Cells and Burkitt Lymphoma Cells: Lack of CD95 (Fas/APO–1) Ligand Expression and Function*, European Journal of Immunology 27(4):1029–34 (Apr., 1997) (Abstract Only).

Denburg, et al., *Nervous System Lupus: Pathogenesis and Rationale for Therapy*, Scandinavian Journal of Rheumatology, 24(5):263–73 (1995) (Abstract Only).

Diaz, et al., *T–lymphocyte Lines Specific for Glutamic Acid Decarboxylase (GAD) the 64K Beta–Cell Antigen of IDDM*, Diabetes 41(1):118–21 (Jan., 1992) (Abstract Only).

Dong, et al., *Quantitative Analysis of the Packaging Capacity of Recombinant Adeno–Associated Virus*, Human Gene Therapy, 7(17):2101–2112 (Nov. 10, 1996) (Abstract Only).

DreEke, et al., *Impact of Natural Killer Cells and Macrophages on the Course of Acute Graft Rejection Following Allogeneic Heart Transplantation in the Rat*, Transplantation Proceedings, 28(6):3259–3260 (Dec., 1996).

Druilhe, et al., *Fas–Mediated Apoptosis in Cultured Human Eosinophils*, Blood, 87(7):2822–2830 (Apr. 1, 1996) (Abstract Only).

Duncan, et al., *Cultured Fibroblasts in Avian Scleroderma, an Autoimmune Fibrotic Disease, Display an Activated Phenotype*, Journal of Autoimmunity 5(5):603–15 (Oct., 1992) (Abstract Only).

During, et al., *Adeno–Associated Virus Vectors for Gene Therapy of Neurodegenerative Disorders*, Clinical Neuroscience, 3(5):292–300 (1995–96) (Abstract Only).

Eck, et al., *The Structure of Tumor Necrosis Factor–Δ at 2.6 A Resolution*, The Journal of Biological Chemistry, 264(29):17595–17604 (Oct. 15, 1989).

Eischen, et al., *Comparison of Apoptosis in Wild–Type and Fas–Resistant Cells: Chemotherapy–Induced Apoptosis Is Not Dependent on Fas/Fas Ligand Interactions*, Blood, 90(3):935–943 (Aug. 1, 1997).

Eischen, et al., *Fc Receptor–Induced Expression of Fas Ligand on Activated NK Cells Facilitates Cell–Mediated Cytotoxicity and Subsequent Autocrine NK Cell Apoptosis*, Journal of Immunology, 156(8):2693–9 (Apr. 15, 1996) (Abstract Only).

Enari, et al., *Apoptosis by a cytosolic extract from Fas–activated cells*, Embo Journal, 14(21):5201–8 (Nov. 1, 1995) (Abstract Only).

Enari, et al., *Different Apoptic Pathways Mediated by Fas and the Tumor–Necrosis–Factor Receptor. Cytosolic Phospholipase A2 is not Involved in Fas–Mediated Apoptosis*, European Journal of Biochemistry, 236(2):533–8 (Mar. 1, 1996) (Abstract Only).

Enari, et al., *Involvement of an ICE–like protease in Fas- –mediated apoptosis*, Nature, 375(6526):78–81 (May 4, 1995) (Abstract Only).

Enari, et al., *Sequential activation of ICE–like and CPP32–like proteases during Fas–mediated apoptosis*, Nature, 380(6576):723–6 (Apr. 25, 1996) (Abstract Only).

Esser, et al., *Distinct T Cell Receptor Signaling Requirments for Perforin–or FasL–Mediated Cytotoxicity*, Journal of Experimental Medicine, 183(4):1697–706 (Apr. 1, 1996) (Abstract Only).

Estaquier, et al., *Fas–mediated apoptosis of CD4+ and CD8+ T cells from human immunodeficiency virus–infected persons: differential in vitro preventive effect of cytokines and protease antagonists*, Blood, 87(12):4959–66 (Jun. 15, 1996) (Abstract Only).

Evans, *An engineererd poliovirus chimaera elicits broadly reactive HIV–1 neutralizing antibodies*, Nature 339:385–388 (Jun., 1989).

Faull, et al., *Inside–out Signaling through Integrins*, Journal of the American Society of Nephrology, 7(8):1091–1097 (Aug., 1996) (Abstract Only).

Ferry, et al., *Sex as a Determining Factor in the Effect of Exercise on In Vivo Autoimmune Response Adjuvant Arthritis*, Journal of Applied Physiology, 76(3):1172–5 (Mar., 1994) (Abstract Only).

Fischer, et al., *A Novel Adenovirus–Adeno–Associated Virus Hybrid Vector That Displays Efficient rescue and delivery of the AAV Genome*, Human Gene Therapy, 7(17):2079–2087 (Nov. 10, 1996) (Abstract Only).

Fisher, et al., *Recombinant Adeno–Associated virus for Muscle Directed Gene Therapy*, Nature Medicine, 3(3):306–312 (Mar., 1997) (Abstract Only).

Fisher–Hoch, et al., *Protection of rhesus monkeys from fatal Lassa fever by vaccination with a recombinant vaccinia virus containing the Lassa virus glycoprotein gene*, Proc. Natl. Acad. Sci., 86:317–321 (Jan., 1989).

Flexner, *Attenuation and immunogenecity in primates of vaccinia virus recombinants expressing human interlukin–2*, Vaccine 8:17–21 (1990).

Frederick, et al., *Protein Tyrosine Kinase Inhibition Blocks Granule Exocytosis and Cytolytic function of Lymphokine–Activated Killer Cells*, Immunopharmacology, 35(2):83–102 (Nov., 1996) (Abstract Only).

French et al., *Fas and Fas Ligand in Embryos and Adult Mice: Ligand Expression in Several Immune–Privileged Tissues and Coexpression in Adult Tissues Characterized by Apoptotic Cell Turnover*, Journal of Cell Biology, 133(2):335–43 (Apr., 1996) (Abstract Only).

Fukuo, et al., *Nitric Oxide Induces Upregulation of Fas and Apoptosis in Vascular Smooth Muscle*, Hypertension, 27(3 Pt 2):823–6 (Mar., 1996) (Abstract Only).

Garner, et al., *Characterization of a Granule–Independent Lytic Mechanism Used by CTL Hybridomas*, 153(12):5413–5421 (Dec. 15, 1994) (Abstract Only).

Garrone, et al., *Fas Litigation Induces Apoptosis of CD40–Activated Human B Lymphocytes*, Journal of Experimental Medicine, 182(5):1265–73 (Nov. 1, 1995) (Abstract Only).

Gauntt, et al., *What Lessons Can be Learned from Animal Model Studies in Viral Heart Disease?*, Scandinavian Journal of Infectious Diseases, Supplementum, 88:49–65 (1993) (Abstract Only).

Genestier, et al., *T Cell Sensitivity to HLA Class I–Mediated Apoptosis is Dependent on Interleukin–2 and Interleukin–4*, European Journal of Immunology, 27(2):495–499 (Feb., 1997) (Abstract Only).

Giordano, et al., *Potential Involvement of Fas and Its Ligand in the Pathogenesis of Hashimoto's Thyroiditis*, Science, 275(5302):960–3 (Feb. 14, 1997) (Abstract Only).

Glass, et al., *Regulation of the Fas Lytic Pathway in Cloned CTL*, Journal of Immunology, 156(10):3638–44 (May 15, 1996) (Abstract Only).

Goillot, et al., *Mitogen–Activated Protein Kinase–Mediated Fas Apoptotic Signaling Pathway*, Proceedings of the National Academy of Sciences of the United States of America, 94(7):3302–3307 (Apr. 1, 1997) (Abstract Only).

Gonzalez–Garcia, et al., *Lck is Necessary and Sufficient for Fas–Ligand Expression and Apoptotic Cell Death in Mature Cycling T Cells*, Journal of Immunology, 158(9):4104–12 (May 1, 1997) (Abstract Only).

Gravestein, et al., *Cloning and Expression of Murine CD27; Comparison With 4–1BB, Another Lymphocyte–Specific Member of the Nerve Growth Factor Receptor Family*, European Journal of Immunology, 23(4):943–950 (Apr., 1993) (Abstract Only).

Griffith, et al., *Fas Ligand–Induced Apoptosis as a Mechanism of Immune Privilege*, Science, 270:1189–92 (Nov. 17, 1995).

Griffith, et al., *The role of FasL–induced apoptosis in immune privilege*, Immunology Today, 18(5):240–244 (May, 1997).

Gruss, et al., *Tumor necrosis factor ligand superfamily: involvement in the pathology of malignant lympohomas*, Blood, 85(12):3378–404 (Jun. 15, 1985) (Abstract Only).

Gumperz, et al., *The enigma of the natural killer cell*, Nature, 378:245–248 (Nov. 16, 1995).

Guy–Grand, et al., *Complexity of the Mouse Gut T Cell Immune System: Identification of Two Distinct Natural Killer T Cell Intraepithelial Lineages*, European Journal of Immunology, 26(9):2248–2256 (Sep., 1996) (Abstract Only).

Hahn, et al., *Mechanism and Biological Significance of CD4–Mediated Cytotoxicity*, Immunological Reviews, 146:57–79 (Aug., 1995) (Abstract Only).

Hahn, et al., *Down–modulation of CD4+ T helper type 2 and type 0 cells by T helper type 1 cells via Fas/Fas–ligand interaction*, European Journal of Immunology, 25(9):2679–85 (Sep., 1995) (Abstract Only).

Hale, et al., *Apoptosis: Molecular Regulation of Cell Death*, European Journal of Biochemistry, 236(1):1–26 (Feb. 15, 1996) (Abstract Only).

Hanabuchi, et al., *Fas and its Ligand in a General Mechanism of T–cell–Mediated Cytotoxicity*, Proceedings of the National Academy of Science of the United States of America, 91(11):4930–4 (May 24, 1994) (Abstract Only).

Hanawa, et al., *Anti–alpha beta T cell receptor antibody prevents the progression of experimental autoimmune myocarditis*, Clinical and Experimental Immunology, 96(3):470–5 (Jun., 1994) (Abstract Only).

Hane, et al., *Interaction of Peptides Derived from the Fas Ligand with the Fyn–SH3 Domain*, Febs Letters, 373(3):265–8 (Oct. 16, 1995) (Abstract Only).

Hardiman, et al., *Molecular Characterization and Modular Analysis of Human MyD88*, Oncogene, 13(11):2467–2475 (Dec. 5, 1996) (Abstract Only).

Hasunuma, et al., *Induction of Fas–Dependent Apoptosis in Synovial Infiltrating Cells in Rheumatoid Arthritis*, International Immunology, 8(10):1595–1602 (Oct., 1996) (Abstract Only).

Hauptman, et al., *Early Cardiac Allograft Failure After Orthotopic Heart Transplantation*, American Heart Journal, 127(1):179–186 (Jan., 1994) (Abstract Only).

Hayashi et al., *Pathogenesis of Sjogren's Syndrome–like Autoimmune Lesions in MRL/lpr Mice*, Pathology International, 44(8):559–68 (Aug., 1994) (Abstract Only).

Hayashi, [*Investigations of various animal models for Sjogren's syndrome*], Nippon Rinsho Japanese Journal of Clinical Medicine, 53(10):2383–8 (Oct., 1995) (Abstract Only).

Hayashi, et al., *Biased T Cell Receptor V Beta Gene Usage During Specific Stages of the Development of Autoimmune Sialadenitis in the MRL/1pr Mouse Model of Sjogren's Syndrome*, Arthritis and Rheumatism, 38(8):1077–84 (Aug., 1995) (Abstract Only).

Heber–Katz, *The Ups and Downs of EAE*, International Reviews of Immunology, 9(4):277–85 (1993) (Abstract Only).

Heusel, et al., *Cytotoxic Lymphocytes Require Granzyme B for the Rapid Induction of DNA Fragmentation and Apoptosis in Allogeneic Target Cells*, Cell, 76:977–987 (Mar. 25, 1994).

Hiromatsu, et al., *Increased Fas antigen expression in murine retrovirus–induced immunodeficiency syndrome, MAIDS*, European Journal of Immunology, 24(10):2446–51 (Oct., 1994) (Abstract Only).

Ito, et al., *Rheumatic Diseases in an MRL Strain of Mice with a Deficit in the Functional Fas ligand*, Arthritis Rheum., 40(6):1054–1063 (Jun., 1997) (Abstract Only).

Itoh, et al., *A novel protein domain required for apoptosis. Mutational analysis of human Fas antigen*, Journal of Biological Chemistry, 268(15):10932–7 (May 25, 1993).

Itoh, et al., *Effect of bcl–2 on Fas antigen–mediated cell death*, Journal of Immunology, 151(2):621–7 (Jul. 15, 1993) (Abstract Only).

Iwai, et al., *Differential Expression of bcl–2 and Susceptibility to Anti–Fas–Mediated Cell Death in Peripheral Blood Lymphocytes, Monocytes, and Neutrophils*, Blood, 84(4):1201–1208 (Aug. 15, 1994) (Abstract Only).

Johnson, et al., *Superantigens: Structure and Relevance to Human Disease*, Proceedings of the Society for Experimental Biology and Medicine, 212(2):99–109 (Jun., 1996) (Abstract Only).

Johnson–Tardieu, et al., *Autoimmune Diabetes–Prone NOD Mice Express the Lyt2 Alpha (Lyt2.1) and Lyt3 Alpha (Lyt3.1) Alleles of CD8*, Immunogenetics, 43(1–2):6–12 (1996) (Abstract Only).

Jones, et al., *Structure of Tumor Necrosis Factor*, Nature, 338:225–228 (Mar. 16, 1989).

Ju, et al., *Fas (CD95)/FasL Interactions Required for Programmed Cell Death After T–Cell Activation*, Nature, 373(6513):444–8 (Feb. 2, 1995) (Abstract Only).

Kadri–Hassani, et al., *Bimodal Action of Fatty Acids on PMA–Stimulated O2. –Production in Human Adherent Monocytes*, Journal of Lipid Mediators and Cell Signalling, 11(2):159–173 (Mar. 11, 1995) (Abstract Only).

Kadri–Hassani, et al., *The Fatty Acid Bimodal Action on Superoxide Anion Production by Human Adherent Monocytes Under Phorbol 12–Myristate 13–Acetate or Diacylglycerol Activation Can be Explained by the Modulation of Protein Kinase C and p47phox Translocation*, Journal of Biological Chemistry, 270(25):15111–15118 (Jun. 23, 1995) (Abstract Only).

Kagi, et al., *Fas and perforin pathways as major mechanisms of T cell–mediated cytotoxicity*, Science, 265(5171):528–30 (Jul. 22, 1994).

Kagi, et al., *Molecular Mechanism of Lymphocyte–Mediated Cytotoxicity and Their Role in Immunological Protection and Pathogenesis in Vivo*, Annual Review of Immunology, 14:207–232 (1996) (Abstract Only).

Kahan, et al., *Potential Applications of Therapeutic Drug Monitoring of Sirolimus Immunosuppression in Clinical Renal Transplantation*, Therapeutic Drug Monitoring, 17(6):672–675 (Dec., 1995) (Abstract Only).

Kang, et al., *Fas ligand expression in islets of Langerhans does not confer immune privilege and instead targets them for rapid destruction*, Nature Medicine, 3(7):738–743 (Jul., 1997).

Kanj, et al., *Cytomegalovirus Infection Following Liver Transplantation: Review of the Literature*, Clinical Infectious Diseases, 22(3):537–549 (Mar., 1996) (Abstract Only).

Karp, et al., *In Vivo Activity of Tumor Necrosis Factor (TNF) Mutants, Secretory but Not Membrane–Bound TNF Mediates the Regression of Retrovirally Transduced Murine Tumor*, The Journal of Immunology, 149(6):2076–2081 (Sep., 15, 1992).

Kawamura, et al., *Cytotoxic Activity Against Tumour Cells Mediated by Intermediate TCR Cells in the Liver and Spleen*, Immunology, 89(1):68–75 (Sep. 1996) (Abstract Only).

Kayagaki, et al., *Metalloproteinase–Mediated Release of Human Fas Ligand*, Nippon Rinsho, Japanese Journal of Clinical Medicine, 54(7):1747–52 (Jul., 1996) (Abstract Only).

Kelly, et al., *Tacrolimus: a New Immuosuprressive Agent*, American Journal of Health–System Pharmacy, 52(14):1521–1535 (Jul. 15, 1995) (Abstract Only).

Khar, et al., *Natural Killer Cell as the Effector Which Mediates in Vivo Apoptosis in AK–5 Tumor Cells*, Cellular Immunology, 117(1):86–92 (Apr. 10, 1997) (Abstract Only).

Kiener, et al., *Differential Induction by Apoptosis by Fas–Fas Ligand Interactions in Human Monocytes and Macrophages*, Journal of Experimental Medicine, 185(8):1511–1516 (Apr. 21, 1997) (Abstract Only).

Kobashi, et al., *Nonsuppurative Cholangitis is Induced in Neonatally Thymectomized Mice: a Possible Animal Mode for Primary Biliary Cirrhosis*, Hepatology, 19(6):1424–30 (Jun., 1994) (Abstract Only).

Koeberl, et al., *Persistent Expression of Human Clotting Factor IX from Mouse Liver After Intravenous Injection of Adeno–Associated Virus Vectors*, Proceedings of the National Academy of Sciences of the United States of America, 94(4):1426–31 (Feb. 18, 1997) (Abstract Only).

Kohn, et al., *Gene Therapy for Haematopoietic and Lymphoid Disorders*, Clinical and Experimental Immunology, 107(Suppl 1):54–7 (Jan., 1997) (Abstract Only).

Koizumi, et al., *Regulation of bcl–xL Expression and Fas Susceptibility in Mouse B Cells by CD40 Ligation, Surface IgM Crosslinking and IL–4*, Molecular Immunology, 33(16):1247–53 (Nov., 1996) (Abstract Only).

Korbutt, et al., *Cotransplantation of Allogeneic Islets With Allogeneic Testicular Cell Aggregates Allows Long–Term Graft Survival Without Systemic Immunosuppression*, Diabetes 46(2):317–322 (Feb., 1997) (Abstract Only).

Korner, et al., *Unimpaired Autoreactive T–Cell Traffic Within the Central Nervous System During Tumor Necrosis Factor Receptor–Mediated Inhibition of Experimental Autoimmune Encephalomyelitis*, Proceedings of the National Academy of Sciences of the United States of America, 92(24):11066–70 (Nov. 21, 1995) (Abstract Only).

Koskinen, et al., *Chronic Rejection*, Current Opinion in Nephrology and Hypertension, 5(3):269–272 (May, 1996) (Abstract Only).

Kosuda, et al., *Mercury–Induced Renal Autoimmunity in BN⇔LEW.1N Chimeric Rats*, Cellular Immunology, 155(1):77–94 (Apr. 15, 1994) (Abstract Only).

Kotake, et al., [New approaches to the regulation of autoimmune disease], Nippon Ganka Gakkai Zasshi. Acta Societatis Ophthalmologicae Japonicae, 98(2):121–129 (Feb., 1994) (Abstract Only).

Kovanecz, et al. *In–Vitro Steroid Sensitivity in Patients with Chronic Uraemia and Renal Transplantation: Possible Association with HLA Phenotypes*, Nephrology, Dialysis, Transplantation, 9(10):1476–1476 (1994) (Abstract Only).

Lagresle, et al., *Regulation of Germinal Center B Cell Differentiation, Role of the Human APO–1/Fas (CD95) Molecule*, The Journal of Immunology, 154(11):5746–5756 (Jun. 1, 1995).

Laochumroonvorapong, et al., *H202 Induces Monocyte Apoptosis and Reduces Viability of Mycobacterium Avium–M. Interacellulare Within Cultured Human Monocytes*, Infection and Immunity 64(2):452–459 (Feb., 1996) (Abstract Only).

Lau, et al., *Prevention of Islet Allograft Rejection with Engineered Myoblasts Expressing FasL in Mice*, Science, 273:109–112 (Jul. 5, 1996).

Laurence, et al., *Plasma from Patients with Idiopathic and Human Immunodeficiency Virus–Associated Thrombotic Thrombocytopenic Purpura Induces Apoptosis in Microvascular Endothelial Cells*, Blood, 87(8):3245–54 (Apr. 15, 1996) (Abstract Only).

Le Deist, et al., *Clinical, Immunological, and pathological consequences of Fas-deficient conditions*, The Lancet, 348:719–723 (Sep. 14, 1996).

Leger, et al., *Modulation by Some Fatty Acids of Protein Kinase C–dependent NADPH Oxidase in Human Adherent Monocyte: Mechanism of Action, Possible Implication in Atherogenesis*, Comptes Rendus des Seances de la Societe de Biologie et de Sesfiliales, 189(5):765–779 (1995) (Abstract Only).

Lens, et al., *A Dual Role for Both CD40–Ligand and TNF–Alpha in Controlling Human B Cell Death*, Journal of Immunology 156(2):507–514 (Jan. 15, 1996).

Lightman, et al., *Effect of Lymphocytic Infiltration on the Blood–Retinal Barrier in Experimental Autoimmune Uveoretinitis*, Clinical and Experimental Immunology, 88(3):473–7 (Jun., 1992) (Abstract Only).

Liu, et al., *Morphologic and Functional Characterization of Perforin–Deficient Lymphokine–activated Killer Cells*, Journal of Immunology 155(2):602–608 (Jul. 15, 1995) (Abstract Only).

Lubovy, et al., *Stable Transduction of Recombinant Aden–Associated Virus Into Hematopoietic Stem Cells From Normal and Sickle Cell Patients*, Biol Blood Marrow Transplant, 2(1):24–30 (Feb., 1996) (Abstract Only).

Lynch, et al., *Fas and FasL in the Homeostatic Regulation of Immune Responses*, Immunology Today, 16(12):569–74 (Dec., 1995) (Abstract Only).

Lynch, et al., *Adeno–Associated Virus Vectors for Vascular Gene Delivery*, Circulation Research, 80(4):497–505 (April, 1997) (Abstract Only).

Lynch, et al., *The Mouse Fas–Ligand Gene is Mutated in gld Mice and Is Part of a TNF Family Gene Cluster*, Immunity, 1:131–136 (May, 1994).

Malik, et al., *Recombinant Adeno–Associated Virus Mediates a High Level of Gene Transfer but Less Efficient Intergration in the K562 Human Hematopoietic Cell Line*, Journal of Virology, 71(3):1776–1783 (Mar., 1997) (Abstract Only).

Marsters, et al., *Activation of Apoptosis by Apo–2 Ligand is Independent of FADD but Blocked by CrmA*, Current Biology, 6(6):750–752 (Jun. 1, 1996) (Abstract Only).

Martin, et al., *Immunological Aspects of Experimental Allergic Encephalomyelitis and Multiple Sclerosis*, Critical Reviews in Clinical Laboratory Sciences, 32(2):121–82 (1995) (Abstract Only).

Martiniello, et al., *Natural Cell–Mediated Cytotoxicity (NCMC) Against NK–Sensitive Tumours in vitro by Murine Splenn Ly–6C+ Natural T Cells*, International Journal of Cancer, 70(4):450–60 (Feb. 7, 1997) (Abstract Only).

Masuko, [*Analysis of T Cell clonality in mice with autoimmune sialoadenitis*], Nippon Rinsho. Japanese Journal of Clinical Medicine, 53(10):2401–6 (Oct. 1995) (Abstract Only).

Matsumoto, et al., *Transfer of Autoimmune Diabetes from Diabetic NOD Mice to NOD Athymic Nude Mice: the Roles of T Cell Subsets in the Pathogenesis*, Cellular Immunology, 148(1):189–97 (Apr. 15, 1993) (Abstract Only).

Maxwell, et al., *Autonomous Parvovirus Transduction of a Gene Under Control of Tissue–Specific or Inducible Promoters*, Gene Therapy, 3(1):28–36 (Jan., 1996) (Abstract Only).

McFarland, et al., *Amelioration of Autoimmune Reactions by Antigen–Induced Apoptosis of T cells*, Advances in Experimental Medicine and Biology, 383:157–66 (1995) (Abstract Only).

McMichael, et al., *Cytotoxic T–Cell Immunity to Influenza*, NE J Med, 309(1):13–17 (Jul., 1983).

Mignot, et al., *Narcolepsy and immunity*, Advances in Neuroimmunology 5(1):23–37 (1995) (Abstract Only).

Miller, et al., *Evolution of the T–Cell Repertoire During the Course of Experimental Immune–Mediated Demyelinating Diseases*, Immunological Reviews, 144:225–44 (Apr. 1995) (Abstract Only).

Miller, *Retrovirus Packaging Cells*, Human Gene Therapy 1:5–14 (1990).

Minegishi, et al., *A Human CD4–CD8–T–Cell Receptor Alpha Beta + T Leukemic Cell Line Undergoing Phytohemagglutinin–Induced Apoptosis*, Leukemia Research, 19(7):433–42 (Jul., 1995) (Abstract Only).

Mita, et al., *Role of Fas Ligand in Apoptosis Induced by Hepatitis C Virus Infection*, Biochemical and Biophysical Research Communications, 204(2):468–474 (Oct. 28, 1994).

Mitra, et al., *HIV–1 Upregulates Fas Ligand Expression in CD+4 T Cells In Vitro and In Vivo: Association with Fas–Mediated Apoptosis and Modulation by Aurintricarboxylic Acid*, Immunology, 87(4):581–5 (Apr. 1996) (Abstract Only).

Montel, et al., *Fas Involvement in Cytotoxicity Mediated by Human NK Cells*, Cellular Immunology, 166(2):236–446 (Dec., 1995) (Abstract Only).

Montel, et al., *Fas–Mediated Cytotoxicity Remains Intact in Perforin and Granzyme B Antisense Transfectants of a Human NK–Like Cell Line*, Cellular Immunology, 165(2):312–317 (Oct. 15, 1995) (Abstract Only).

Mor, et al., *Experimental Aspects of T Cell Vaccination*, Clinical and Experimental Rheumatology, 11(Suppl. 8):S55–7 (Mar.–Apr., 1993) (Abstract Only).

Mor, et al., *Pathogenicity of T Cells Responsive to Diverse Cryptic Epitopes of Myelin Basis Protein in the Lewis Rat*, Journal of Immunology, 155(7):3693–9 (Oct. 1, 1995) (Abstract Only).

Morlion, et al., *The Effects of Parenteral Fish Oil on Leukocyte Membrane Fatty Acid Composition and Leukotriene–Synthesizing Capacity in Patients With Postoperative Trauma*, Metabolism: Clinical and Experimental, 45(10):1208–1213 (Oct., 1996) (Abstract Only).

Mountz, et al., *Autoimmune Disease. A Problem of Defective Apoptosis*, Arthritis Rheum, 37(10):1415–1420 (Oct., 1994) (Abstract Only).

Moustaid, et al., *Insulin Increases Lipogenic Enzyme Activity in Human Adipocytes in Primary Culture*, Journal of Nutrition, 126(4):865–870 (Apr., 1996) (Abstract Only).

Muller, et al., *Clonal Deletion of Major Histocompatibility Complex Class I–Restricted CD4+CD8+ Thymocytes in Vitro is Independent of the CD95 (APO–1/Fas) Ligand*, European Journal of Immunology, 25(10):2996–9 (Oct., 1995).

Muller–Ladner, et al., *Oncogenes in Rheumatoid Arthritis*, Rheumatic Diseases Clinics of North America, 21(3):675–90 (Aug. 21, 1995) (Abstract Only).

Nabel, et al., *Transduction of a Foreign Histocompatibility Gene into the Arterial Wall Induces Vasculitis*, Proceedings of the National Academy of Sciences of the United States of America, 89(11):5157–61 (Jun. 1, 1992).

Nagata, *Fas and Fas Ligand: A Death Factor and Its Receptor*, Advances in Immunology, 57:129–144 (1994).

Nagata, *Apoptosis Regulated by a Death Factor and its Receptor: Fas Ligand and Fas. Philosophical Transactions of the Royal Society of London. Series B*, Biological Science, 345(1313):281–287 (Aug. 30, 1994) (Abstract Only).

Nagata, et al., *Fas and Fas ligand; lpr and gld mutations*, Immunology Today, 16(1):39–43 (Jan., 1995) (Abstract Only).

Nagata, et al., *The Fas death factor*, Science, 267(5203):1449–56 (Mar. 10, 1995).

Nagata, et al., *Mutations in the Fas antigen gene in lpr mice*, Seminars in Immunology, 6(1):3–8 (Feb. 1994) (Abstract Only).

Nagler, et al., *Granulocyte–Macrophage Colony–Stimulating Factor Dependent Monocyte–Mediated Cytotoxicity Post–Autologous Bone Marrow Transplantation*, Leukemia Research, 20(8):637–643 (Aug., 1996) (Abstract Only).

Ni, et al., *Fas–mediated apoptosis in primary cultured mouse hepatocytes*, Experimental Cell Research, 215(2):332–7 (Dec. 1994) (Abstract Only).

Nicoletti, et al., *Effects of Sodium Fusidate in Animal Models of Insulin–Dependent Diabetes Mellitus and Septic Shock*, Immunology, 85(4):645–50 (Aug., 1995) (Abstract Only).

Nishimura, et al., *Fas Antigen Expression in Brains of Patients with Alzheimer–Type Dementia*, Brain Research, 695(2):137–45 (Oct. 16, 1995) (Abstract Only).

Ogasawara, et al., *Selective Apoptosis of CD4+CD8+ Thymocytes by the Anti–Fas Antibody*, Journal of Experimental Medicine, 181(2):485–491 (Feb. 1, 1995) (Abstract Only).

Ogasawara, et al., *Lethal Effect of the Anti–Fas Antibody in Mice*, [published erratum appears in Nature 365(6446):568] Nature, 364(6440):806–9 (Aug. 26, 1993) (Abstract Only).

Ohtsuru, et al., *'Split Tolerance' Induction by Intrathymic Injection of Acetylcholine Receptor in a Rat Model of Autoimmune Myasthenia Gravis; Implications for the Design of Specific Immunotherapies*, Clinical and Experimental Immunology, 102(3):462–7 (Dec., 1995) (Abstract Only).

Oka, et al., *Immunosuprression in Organ Transplantation*, Japanese Journal of Pharmacology, 71(2):89–100 (Jun., 1996) (Abstract Only).

Okada, et al., *Gene Therapy Against an Experimental Glioma Using Adeno–Associated Virus Vectors*, Gene Therapy, 3(11):957–964 (Nov., 1996) (Abstract Only).

Okazawa, et al., *Bcl–2 Inhibits Retinoic Acid–Induced Apoptosis During the Neural Differentiation of Embryonal Stem Cells*, Journal of Cell Biology, 132(5):955–68 (Mar., 1996) (Abstract Only).

Okumura, et al., *Oral Administration of Acetylcholine Receptor: Effects on Experimental Myasthenia Gravis*, Annals of Neurology, 36(5):704–13 (Nov., 1994) (Abstract Only).

Olive, *T Cell Receptor Usage in Autoimmune Disease*, Immunology and Cell Biology, 73(4):297–307 (Aug., 1995) (Abstract Only).

Onodera, et al., *Upregulation of Bcl–2 Protein in the Myasthenic Thymus*, Annals of Neurology, 39(4):521–8 (Apr., 1996) (Abstract Only).

Ortaldo, et al., *Fas Involvement in Human NK Cell Apoptosisi: Lack of a Requirement for CD16–Mediated Events*, Journal of Leukocyte Biology, 61(2):209–215 (Feb., 1997) (Abstract Only).

Oshimi, et al., *Involvement of Fas Ligand and Fas–Mediated Pathway in theCytotoxicity of Human Natural Killer Cells*, 157(7):2909–2915 (Oct. 1, 1996) (Abstract Only).

Oshimi, et al., *Necrosis and Apoptosis Associated with Distinct Ca2+ Response Patterns in Target Cells Attacked by Human Natural Killer Cells*, Journal of Physiology, 495(Pt 2):319–329 (Sep. 1, 1996) (Abstract Only).

Oyaizu, et al., *Requirement of p56lck in T–Cell Receptor/CD3–Mediated Apoptosis and Fas–Ligand Induction in Jurkat Cells*, Biochemical and Biophysical Research Communications, 213(3):994–1001 (Aug. 24, 1995) (Abstract Only).

Ozdemirli, et al., *Fas (CD95)/Fas Ligand Interactions Regulate Antigen–Specific, Major Histocompatibility Complex–Restricted T/B Cell Proliferative Responses*, European Journal of Immunology, 26(2):415–9 (Feb. 1996) (Abstract Only).

Pappo, et al., *Human Polyoma Virus Infection of Renal Allografts: Histopathologic Diagnosis, Clinical Significance, and Literature Review*, Modern Pathology, 9(2):105–109 (Feb. 9, 1996) (Abstract Only).

Park, et al., *A Novel Gene Product that Couples TCR Signaling to FAS (CD95) Expression in Activation–Induced Cell Death,*. Immunity, 4(6):583–91 (Jun., 1996) (Abstract Only).

Patselas, et al., *Role of Natural Killer and Killer Cells in Concordant Xenograft Rejection*, Transplantation Proceedings, 27(1):262–263 (Feb., 1995) (Abstract Only).

Paul, *Chronic Renal Transplant Loss*, Kidney International, 47(6):1491–1499 (Jun., 1995) (Abstract Only).

Pearson, et al., *CTLA4–Ig Plus Bone Marrow Induces Long–Term Allograft Survivial and donor Specific Unresponsiveness in the Murine Model. Evidence for Hematopoietic Chimerism*, Transplantation, 61(7):997–1004 (Apr. 15, 1996) (Abstract Only).

Phillips, *Antisense Inhibition and Adeno–Associated Viral Vector Delivery for Reducing Hypertension*, Hypertension 29(1 Pt 2):177–87 (Jan., 1997) (Abstract Only).

Phillips, et al., *Prolonged Reduction of High Blood Pressure With an In Vivo, Nonpathogenic, Adeno–Associated Viral Vector Delivery of AT1–R mRNA Antisense*, Hypertension, 29(1 Pt 2): 374–380 (Jan., 1997) (Abstract Only).

Pitti, et al., *Induction of Apoptosis by Apo–2 Ligand, a New Member of the Tumor Necrosis Factor Cytokine Family*, The Journal of Biological Chemistry, 271(22):12687–12690 (May 31, 1996).

Platt, *Xenotransplantation: recent progress and current perspectives*, Current Opinion in Immunology, 8(5):721–728 (Oct., 1996) (Abstract Only).

Ponnazhagan, et al., *Adeno–Associated Virus Type 2–Mediated Transduction of Murine Hematopoietic Cells With Long–Term Repopulating Ability and Sustained Expression of a Human Globin Gene In Vivo*, Journal of Virology, 71(4):3098–3104 (Apr. 1997) (Abstract Only).

Posner, et al., *Early Results of Infrageniculate Arterial Reconstruction Using Cryopreserved Homograft Saphenous Conduit (CADVEIN) and Combination Low–Dose Systemic Immunosuppression*, Journal of the American College of Surgeons, 183(3):208–216 (Sep., 1996) (Abstract Only).

Pratt, et al., *Allograft Immune Response with sCR1 Intervention*, Transplant Immunology, 4(1):72–75 (Mar., 1996) (Abstract Only).

Ramanathan, et al., *Alcohol inhibits cell–cell adhesion mediated by human L1*, Journal of Cell Biology, 133(3):381–90 (Apr., 1996) (Abstract Only).

Rashba et al., *Type 1 Diabetes Mellitus: An Inbalance Between Effector and Regulatory T Cells?*, Acta Diabetologica, 30(2):61–9 (1993) (Abstract Only).

Razvi, et al., *Lymphocyte Apoptosis During the Silencing of the Immune Response to Acute Viral Infections in Normal, Lpr, and Bcl–2–Transgenic Mice*, American Journal of Pathology, 147(1):79–91 (Jul. 1995) (Abstract Only).

Reber, et al., *Prolactin and Immunomodulation*, American Journal of Medicine, 95(6):637–644 (Dec., 1993) (Abstract Only).

Renno, et al., *Peripheral T cells undergoing superantigen–induced apoptosis in vivo express B220 and upregulate Fas and Fas ligand*, Journal of Experimental Medicine, 183(2):431–437 (Feb. 1, 1996) (Abstract Only).

Rhim, et al., *Autoimmune Disease of the Ovary Induced by a ZP3 Peptide from the Mouce Zona Pellucida*, Journal of Clinical Investigation, 89(1):28–35 (Jan., 1992) (Abstract Only).

Richardson, et al., *Fas Ligation Triggers Apoptosis in Macrophages but not Endothelial Cells*, European Journal if Immunology, 24(11):2640–2645 (Nov., 1994) (Abstract Only).

Roberge, et al., *Treatment of autoimmune uveoretinitis in the rat with rapamycin, an inhibitor of lymphpcyte growth factor signal transduction*, Current Eye Research, 12(2):197–203 (Feb., 1993) (Abstract Only).

Robertson, et al., Functional Consequences of APO–1/Fas (CD95) Antigen Expression by Normal and Neoplastic Hematopoietic Cells, Leukemia and Lymphoma, 17(1–2):51–61 (Mar. 1995) (Abstract Only).

Rosenfeld, et al., Adenovirus–Mediated Transfer of a Recombinant 1–Antitrypsin Gene to the Lung Epithelium in Vivo, Science 252:431–434 (Apr. 19, 1991).

Ross, et al., Cytokine–Induced Apoptosis of Human Natural Killer Cells Identifies a Novel Mechanism to Regulate the Innate Immune Response, Blood, 89(3):910–918 (Feb. 1, 1997) (Abstract Only).

Rostami, Guillain–Barre Syndrome: Clinical and Immunological Aspects, Springer Seminars in Immunopathology, 17(1):29–42 (1995) (Abstract Only).

Roth, et al., Immunochemotherapy of Malignant Glioma; Synergistic Activity of CD95 Ligand and Chemotherapeutics, Cancer Immunology, Immunotherapy, 44(1):55–63 (Mar., 1997) (Abstract Only).

Russell, Activation–Induced Death of Mature T Cells in the Regulation of Immune Responses, Current Opinion in Immunology, 7(3):382–8 (Jun. 1995) (Abstract Only).

Saas, et al., Fas Ligand expression by Astrocytoma in vivo: Maintaining Immune Privilege in the Brain?

Sabin, et al., History of Sabin attenuated poliovirus oral live vaccine strains, J. Biol. Standardization 1:115–118 (1973).

Salmon, et al., The Progressive Differentiation of Primed T Cells is Associated With An Increasing Susceptibility to Apoptosis, European Journal Immunology, 24(4):892–899 (Apr., 1994) (Abstract Only).

Sasao, et al., Fas Antigen (CD95) Expressions and Apoptosis of Neoplastic Cells From Various Lymphoid Malignancies Including Adult T–Cell Leukemia/Lymphoma, Nippon Rinsho, Japanese Journal of Clinical Medicine, 54(7):1986–91 (Jul., 1996) (Abstract Only).

Sato, et al., An Aggressive Nasal Lymphoma Accompanied by High Levels of Soluble Fas Ligand, British Journal of Haematology, 94(2):379–382 (Aug., 1996) (Abstract Only).

Schuler, et al., Dendritic cells: from ignored cells to major players in T–cell–mediated immunity, Int Arch Allergy Immunol, 112(4):317–322 (Apr., 1997) (Abstract Only).

Schulze–Osthoff, et al., Cell Nucleus and DNA Fragmentation are not Required for Apoptosis. Journal of Cell Biology, 127(1):15–20 (Oct., 1994) (Abstract Only).

Shimizu, et al., A Trial to Kill Tumor Cells Through Fas (CD95) –Mediated Apoptosis in Vivo, Biochemical and Biophysical Research Communications, 228(2):375–9 (Nov. 12, 1996) (Abstract Only).

Signore, et al., Retroviruses and Diabetes in Animal Models: Hypothesis for the Induction of the Disease, Diabete et Metabolisme, 21(3):147–55 (Jun., 1955) (Abstract Only).

Silvestris, et al., Autoreactivity in HIV–1 Infection: The Role of Molecular Mimicry, Clinical Immunology and Immunopathology, 75(3):197–205 (Jun., 1995) (Abstract Only).

Silvestris, et al., Antiphosphatidylserine Antibodies in Human Immunodeficiency Virus–1 Patients With Evidence of T–Cell Apoptosis amd Mediate Antibody–Dependent Cellular Cytotoxicity, Blood, 87(12):5185–95 (Jun. 15, 1987) (Abstract Only).

Simmons, et al., Lymphocytes Utilise Sialylated Surface Molecules to Accumulate in Developing Lesions of Autoimmune Encephalomyelitis, Autoimmunity, 14(1):17–21 (1992) (Abstract Only).

Simon, et al., Expansion of Cytokine–Producing CD4–CD8–T Cells Associated with Abnormal Fas Expression and Hypereosinophilia, Journal of Experimental Medicine, 183(3):1071–82 (Mar. 1, 1996) (Abstract Only).

Singer, et al., Apoptosis, Fas and systemic autoimmunity: the MRL–lpr/lpr model, Curr Opin Immunol, 6(6):913–920 Dec., 1994 (Abstract Only).

Sinkovics et al., Can Virus Therapy of Human Cancer be Improved by Apoptosis Induction?, Medical Hypotheses, 44(5):359–68 (May 1995) (Abstract Only).

Smilek, et al., EAE: A Model for Immune Intervention with Synthetic Peptides, International Reviews of Immunology, 9(3):223–30 (1992).

Smoyer, et al., Inherited Interstitial Nephritis in kdkd Mice, International Reviews of Immunology, 11(3):245–51 (1994) (Abstract Only).

Sneller, et al., Clinical, Immunologic, and Genetic Features of an Autoimmune Lymphoproliferative Syndrome Associated with Abnormal Lymphocyte Apoptosis, Blood 89(4):1341–1348 (Feb. 15, 1997) (Abstract Only).

Sobel, et al., Correction if gld Autoimmunity by Co–Infusion of Normal Bone Marrow Suggests that gld is a Mutation of the Fas ligand Gene, 5(10):1275–1278 (Oct., 1993).

Sobel, et al., Co–Infusion of Normal Bone Marrow Partially Corrects the gld T–cell Defect. Evidence for an Intrinsic and Extrinsic Role for Fas Ligand, Journal of Immunology, 154(1):459–64 (Jan. 1, 1995) (Abstract Only).

Soliman, et al., Graves' Disease in Severe Combined Immunodeficient Mice, Journal of Clinical Endocrinology and Metabolism, 80(10):2848–55 (Oct., 1955) (Abstract Only).

Strasser, Life and Death During Lymphocyte Development and Function: Evidence for Two Distinct Killing Mechanisms, Current Opinion in Immunology, 7(2):228–34 (Apr., 1995) (Abstract Only).

Streilein, Unraveling Immune Privilege, Science, 270:1158–1159 (Nov. 17, 1995).

Stryer, Biochemistry 236–249 (1975) W.H. Freeman and Co., San Francisco.

Su, et al., Hematopoietic Cell Protein–Tyrosine Phosphate–Deficient Motheaten Mice Exhibit T Cell Apoptosis Defect, Journal of Immunology, 156(11):4198–208 (Jun. 1, 1996) (Abstract Only).

Suda, et al., Expression of the Fas ligand in cells of T cell lineage, The Journal of Immunology, 154(8):3806–13 (Apr., 15, 1995).

Suda, et al., Molecular Cloning and Expression of the Fas ligand, a Novel Member of the Tumor Necrosis Factor Family, Cell, 75:1169–78 (Dec. 17, 1993).

Suda, et al., Purification and characterization of the Fas–ligand that induces apoptosis, Journal of Experimental Medicine, 179(3):873–9 (Mar. 1, 1994) (Abstract Only).

Sung, et al., The Role of Apoptosis in Antibody–Dependent Cell–Mediated Cytotoxicity Against Monolayers of Human Squamous Cell Carcinoma of the Head and Neck Targets, Cellular Immunology 171(1):20–9 (Jul.10, 1996) (Abstract Only).

Suss, et al., A Subclass of Dendritic Cells Kills CD4 T Cells via Fas/Fas–Ligand–Induced Apoptosis, Journal of Experimental Medicine, 183(4):1789–96 (Apr. 1, 1996) (Abstract Only).

Suthanthiran, et al., Immunosuppressants: Cellular and Molecular Mechanisms of Action, American Journal of Kidney Diseases, 28(2):159–172 (Aug., 1996) (Abstract Only).

Suzuki et al., Mechanism of the Induction of Autoimmune Disease by Graft–Versus–Host Reaction. Role of CD8+ Cells in the Development of Hepatic and Ductal Lesions Induced by CD4+ Cells in MHC Class I Plus II–Different Host, Laboratory Investigation, 70(5):609–19 (May, 1994) (Abstract Only).

Swinnen, et al., Androgens Stimulate Fatty Acid Synthase in the Human Prostate Cancer Cell Line LNCaP, Cancer Research, 57(6):1086–90 (Mar. 15, 1997) (Abstract Only).

Takahashi, et al., Generalized Lymphoproliferative Disease in Mice, Caused by a Point Mutation in the Fas Ligand, Cell, 76(6):969–976 (Mar. 25, 1994) (Abstract Only).

Takahashi, et al., Human Fas ligand: gene stucture, chromosomal location and species specificity International Immunology, 6(10):1567–74 (Oct., 1994).

Takahashi, et al., Mechanism of the development of autoimmune dacryodenitis in the mouse model for primary Sjogren's syndrome, Cellular Immunology, 170(1):54–62 (May 25, 1996) (Abstract Only).

Tanaka, et al., Expression of the functional soluble form of human Fas ligand in activated lymphocytes, The EMBO Journal, 14(6):1129–1135 (1995).

Tanaka, et al., Fas ligand in Human Serum, Nature Medicine, 2(3):317–22 (Mar. 2, 1996) (Abstract Only).

Taniguchi, et al., V alpha 14+ NK T Cells; a Novel Lymphoid Cell Lineage With Regulatory Function, Journal of Allergy and Clinical Immunology, 98(6 Pt 2):S263–269 (Dec., 1996) (Abstract Only).

Troppmann, et al., Discordant Xenoislets from a Large Animal Donor Undergo Accelerated Graft Failure Rather than Hyperacute Rejection: Impact of Immunosuprression, Islet Mass, and Transplant Site on Early Outcome, Surgery, 121(2):194–205 (Abstract Only).

Tsutsui, et al., IFN–Gamma–Induced Factor Up–Regulates Fas Ligand–Mediated Cytotoxic Activity of Murine Natural Killer Cell Clones, 157(9):3967–73 (Nov.1, 1996) (Abstract Only).

Tuosto, et al., Differential Susceptibility to Monomeric HIV gp120–Mediated Apoptosis in Antigen–Activated CD4+ T Cell Populations, European Journal of Immunology, 25(10):2907–2916 (Oct., 1995) (Abstract Only).

Um, et al., Fas Mediates Apoptosis in Human Monocytes by a Reactive Oxygen Intermediate Dependent Pathway, Journal of Immunology, 156(9):3469–3477 (May 1, 1996) (Abstract Only).

Uslu, et al., Sensitization of Human Ovarian Tumor Cells by Subtoxic CDDP to Anti–Fas Antibody–Mediated Cytotoxicity and Apoptosis, Gynecologic Oncology, 62(2):282–91 (Aug., 1996) (Abstract Only).

Van Den Broek, et al., Decreased Tumor Surveillance in Perforin–Deficient Mice, Journal of Experimental Medicine, 184(5):1781–90 (Nov. 1, 1996) Abstract Only).

Van Parijs, et al., The Roles of Costimulation and Fas in T Cell Apoptosis and Peripheral Tolarance, Immunity, 4(3):321–8 (Mar., 1996) (Abstract Only).

Vaux, et al., An Evolutionary Perspective on Apoptosis, Cell, 76:777–779 (Mar. 11, 1994).

Vaux, Ways around rejection, Nature, 377:576–577 (Oct. 19, 1995).

Vincent, et al., Analysis of Recombinant Adeno–Associated Virus Packaging and Requirements for Rep and Cap Gene Products, Journal of Virology, 71(3):1897–905 (Mar., 1997) (Abstract Only).

Wagoner, et al., Cyclophosphamide in Cardiac Transplant Recipients with Frequent Rejection: a Six–Year Retrospective Review, Clinical Transplantation, 10(5):437–443 (Oct., 1996) (Abstract Only).

Walsh, et al., Immune Function in Mice Lacking the Perforin Gene, Proceedings of the National Academy of Sciences of the United States of America, 91(23):10854–10858 (Nov. 8, 1994) (Abstract Only).

Wang, et al., Expression and Function of Fas Antigen on Activated Murine B Cells, European Journal of Immuunology, 26(1):92–6 (Jan., 1996) (Abstract Only).

Warner, et al., Induction of HIV–Specific CTL and Antibody Responses in Mice Using Retroviral Vector–Transduced Cells, AIDS Res. And Human Retroviruses 7(8):645–655, (1991).

Watanabe. et al., Constitutive activation of the Fas ligand gene in mouse lymphoproliferative disorders, Embo Journal, 14(1):12–8 (Jan. 3, 1995) (Abstract Only).

Wantanabe–Fukunaga, et al., Lymphoproliferation Disorder in Mice Explained by Defects in Fas Antigen that Mediates Apoptosis, Nature, 356(6367):314–317 (Mar. 26, 1992) (Abstract Only).

Wantanabe–Fukunaga, et al., The cDNA Structure, Expression, and Chromosomal Assignment of the Mouse Fas Antigen, Journal of Immunology, 148(4):1274–9 (Feb. 15, 1992) (Abstract Only).

Weis, et al., Cellular Events in Fas/APO–1–Mediated Apoptosis in JURKAT T Lymphocytes, Experimental Cell Research, 219(2):699–708 (Aug., 1995) (Abstract Only).

Williams et al., Immunology of Multiple Sclerosis, Clinical Neuroscience, 2(3–4):229–45 (1994) (Abstract Only).

Wilson, et al., The Fas–Fas Ligand System and Other Modulators of Apoptosis in the Cornea, Investigative Ophthalmology and Visual Science, 37(8):1582–92 (Jul., 1996) (Abstract Only).

Wood, Peripheral Tolerance to Alloantigen: Strategies for the Future, European Journal of Immunogenetics, 20(5):439–449 (Oct. 1993) (Abstract Only).

Woodle, et al., Anti–Human Class I MHC Antibodies Induce Apoptosis by a Pathway that is Distinct from the Fas Antigen–Mediated Pathway, Journal of Immunology 158(5):2156–2164 (Mar. 1, 1997) (Abstract Only).

Wu, et al., Fas Ligand Mutation in a Patient with Systemic Lupus Erythematosus and Lymphoproliferative Disease, J. Clin. Invest., 98(5):1107–1113 (Sep., 1996).

Wu, et al., Requirement of Fas (CD95), CD45, and CD11a/ CD18 in Monocyte–Dependant Apoptosis of Human T Cells, Journal of Immunology, 157(2): 707–713 (Jul. 15, 1996) (Abstract Only).

Wu, et al., Targeting Genes: Delivery and Persistent Expression of a Foreign Gene Driven by Mammalian Regulatory Elements in Vivo, J. Biol. Chem. 264:16985–16987 (1989).

Yamauchi, et al., Target Cell–Induced Apoptosis of Interleukin–2–Activated Human Natural Killer Cells: Roles of Cell Surface Molecules and Intracellular Events, Blood, 87(12):5127–35 (Jun. 15, 1987) (Abstract Only).

Yap, et al., Transfer of specific cytotoxic T lymphocytes protects mice inoculated with influenza virus, Nature, 273:238–239 (May, 1978).

Yasutomo, et al., Defective T Cells from gld mice play a pivotal role in development of Thy–1.2+B220+ cells and

*autoimmunity*, Journal of Immunology, 153(12):5855–64 (Dec. 15, 1994) (Abstract Only).

Yokohama, *et al., [The pathogenic mechanism of experimental autoimmune encephalomyelitis and approach for new immunological therapy]*, Nippon rinsho. Japanese Journal of Clinical Medicine, 52(11):3013–8 (Nov., 1994) (Abstract Only).

Yoo, *et al., Cloning and Characterization of the Bovine Fas*, DNA and Cell Biology, 15(3):227–34 (Mar., 1996) (Abstract Only).

Yoo, *et al., Genomic Organization and Chromosomal Mapping of the Bovine Fas/APO–1 Gene*. DNA and Cell Biology 15(5):377–85 (May, 1996) (Abstract Only).

Young, *et al., Characterization of Autoreactive Helper T Cells in a Murine Model of Autoimmune Haemolytic Disease*, Immunology, 80(1):13–21 (Sep., 1983) (Abstract Only).

Zhang, *et al., Suppression of Experimental Autoimmune Myasthenia Gravis after CD8 Depletion is Associated with Decreased IFN–Gamma and IL–4*, Scandinavian Journal of Immunology, 42(4):457–65 (Oct., 1995) (Abstract Only).

Zhang, *et al., Characterzation of Apoptosis –Resistant Antigen–Specific T Cells in Vivo*, Journal of Experimental Medicine, 183(5):2065–73 (May 1, 1996) (Abstract Only).

Zoller, *et al., Interactions Between Cardiomyocytes and Lymphocytes in Tissue Culture: an In Vitro Model of Inflammatory Heart Disease*, Journal of Molecular and Cellular Cardiology, 26(5):627–38 (May, 1994) (Abstract Only).

Zornig, *et al., Loss of Fas/Apo–1 Receptor Accelerates Lymphomagenesis in E mu L–MYC Transgenic Mice but not in animals infected with MoMuLV*, Oncogene, 10(12):2397–2401 (Jun. 15, 1995) (Abstract Only).

* cited by examiner

MUTANT FORMS OF FAS LIGAND AND USES THEREOF

This application is related to provisional application Serial No. 60/039,972, filed Feb. 10, 1997, which is a continuation-in-part of provisional application Serial No. 60/030,871 filed Nov. 13, 1996, from which priority is claimed under 35 U.S.C. §119(e)(1) and which are hereby incorporated herein by reference in their entirety.

FIELD OF THE INVENTION

The invention relates to Fas ligand muteins and chimeric proteins that act as Fas ligand agonists, and the DNA encoding the same. More particularly, the present invention relates to novel forms of Fas ligand, which when expressed in a transformed host cell, are surface bound in a conventional type II prohormone form but non-cleavable therefrom. These non-cleavable forms of Fas ligand and the transformed host cells expressing them are useful in diagnostic assays and in reducing populations of Fas expressing cells (e.g., activated T cells and activated B cells) both in vitro and in vivo. The Fas ligand and transformed host cells of the present invention are particularly useful as pharmaceutical agents in the treatment of transplant rejection and the various autoinmmune diseases that are well known in the art.

BACKGROUND OF THE INVENTION

The tumor necrosis factor superfamily includes ligands that bind the corresponding members of the tumor necrosis factor receptor superfamily of receptors. Such members of the receptor superfamily include, for example, tumor necrosis factor receptors (TNFR) (type I or 55K or TNFR60 and type II or 75K or TNFR80), CD30, nerve growth factor receptor, CD27, CD40, CD95/APO-1 or Fas, CD120a, CD120b, lymphtoxin beta receptor (LT beta R), and a TRAIL receptor. The receptors of this family are membrane bound and recognize soluble or membrane bound ligands that mediate diverse cellular responses. The corresponding ligands for these receptors include in some cases membrane or soluble forms and include, for example, tumor necrosis factor alpha (TNFα), CD30 ligand, nerve growth factor, CD70/CD27 ligand, CD40 ligand, Fas ligand, and TNF-related apoptosis-inducing ligand TRAIL (as described in Wiley et al, Immunity 3:673–82 (1995)). The ligands of the superfamily, including Fas ligand, are type II transmembrane glycoproteins with beta strands that form a jelly-roll beta-sandwich as described in Lotz et al, *J. of Leukocyte Biol* 60: 1–7 (1996), which is hereby incorporated by reference. Treatment of autoimmune diseases present a unique challenge to molecular biology and medical research. Autoimmune diseases affect between 5 and 7% of the human population, often causing chronic debilitating illnesses, as described in Kuby, IMMUNOLOGY, (W.H. Freeman, NY 1992).

Although precise details of an autoimmune response are incompletely understood, the outcome of antigenic stimulation, whether antibody formation or activated T-cells, or tolerance, seems to depend on the same factors whether a reaction to auto-antigen or exogenous antigen, as described in THE MERCK MANUAL, 16th edition (Merck & Co. Inc. 1992). Also described in THE MERCK MANUAL are four classes of auto-antigens. Class 1 is antigens from intracellular regions of the cells of the body that, by virtue of their sequestration from the immune system, are not recognized as "self" in the body once secreted. For example, sympathetic ophthalmia causes the release of eye antigens, and a subsequent self reaction to the antigen. Class 2 is represented by self antigens that may become immunogenic by chemical, physical, or biological alteration, for example, when a chemical couples to a self antigen and produces a "foreign" reaction, for example in contact dermatitis and hypersensitivity to drugs. Class 3 is represented by foreign antigen that cross reacts with self antigen, and induces a self reaction to the self antigen, for example, as shown with the development of encephalitis after rabies vaccination. Class 4 is represented by a mutation in immunoincompetent cells, such as the autoimmune phenomena seen with mammals having lymphoma. Finally, an autoimmune reaction may be epiphenomena, developing secondarily after an immune response to an obscure antigen, for example, a virus. All autoimmune diseases have in common an involvement of the immune system, and many involve either activated B-cells, activated T-cells, or both.

Although various ameliorative and palliative therapies exist for some autoimmune diseases, and while the autoimmune diseases can spontaneously regress in a remission, effective treatment has yet to be developed for treating autoimmune diseases. It would be desirable to advance the capacity of medical and clinical research to develop effective treatments of autoimmune diseases by discovery of new methods and new therapeutic agents targeting the molecular biology of autoimmune diseases.

SUMMARY OF THE INVENTION

The present invention has multiple aspects. In a first aspect, the present invention is directed to non-cleavable forms of Fas ligand, including Fas ligand muteins and Fas ligand chimeras, and to the polynucleotides encoding them. Preferably, the Fas ligand deletion mutein comprises an effective length of the transmembrane region of Fas ligand up to residue 129 of SEQ ID NO: 12 linked by a substantially non-cleavable peptide linkage to the Fas binding domain of human Fas ligand begining from about residue 139 to residue 146 of SEQ ID NO: 12, and the Fas ligand chimera comprises the transmembrane region of a cell surface protein linked by a substantially non-cleavable peptide linkage to the Fas binding domain of human Fas ligand begining from about residue 139 to residue 146 of SEQ ID NO: 12.

A second aspect is directed to a vector (DNA or RNA) comprising a promoter operably linked to a gene encoding a Fas ligand mutein or chimera that when membrane bound is substantially non-cleavable. Preferably, the vector comprises a promoter operably linked to a recombinant gene encoding a Fas ligand deletion mutein or a Fas ligand chimera, the Fas ligand deletion mutein comprising an effective length of the transmembrane region of Fas ligand up to residue 129 of SEQ ID NO: 12 linked by a substantially non-cleavable peptide linkage to the Fas binding domain of human Fas ligand begining from about residue 139 to residue 146 of SEQ ID NO: 12, said Fas ligand chimera comprising the transmembrane region of a cell surface protein linked by a substantially non-cleavable peptide linkage to the Fas binding domain of human Fas ligand begining from about residue 139 to residue 146 of SEQ ID NO: 12.

A third aspect is directed to a transformed host cell, wherein the host cell is transformed with vector (DNA or RNA) encoding a Fas ligand mutein or chimeric protein that when expressed in the cell remains membrane bound.

A fourth aspect of the present invention is directed to compositions comprising the above described host cell and a carrier. In a preferred embodiment, the composition is a pharmaceutical composition and the carrier is a pharmaceutically acceptable carrier.

Another aspect of the present invention is directed to a method for determining the presence in a sample of cells expressing Fas, the method comprising the steps of:
 a) providing a transformed cell having a recombinant Fas ligand surface bound thereto, said surface bound, recombinant Fas ligand being resistant to cleavage;
 b) contacting said transformed cell with a sample containing cells suspected of having surface bound Fas thereon to obtain a cell mixture;
 c) allowing said cell bound Fas to bind to said surface bound recombinant Fas ligand; and
 d) observing said cell mixture for rosette formation or clumping, whereby the binding of cells from said sample to said transformed cell indicates the presence of Fas on the surface of cells in said sample.

In another aspect, the present invention is directed to a method for reducing a population of Fas expressing cells, the method comprising the steps of:
 a) providing a transformed cell having a recombinant Fas ligand surface bound thereto, said surface bound, recombinant Fas ligand being resistant to cleavage; and
 b) contacting a population of Fas expressing cells with said transformed cell, whereby said Fas ligand binds to Fas on said Fas expressing cells, causing said Fas expressing cells that are so bound to undergo apoptosis such that said population is reduced.

In a preferred embodiment of the above method, the Fas expressing cells are activated T cells and/or B cells and said transformed cell expresses a second ligand that is recognized by said activated T cell and/or B cell.

In another aspect, the present invention is directed to a method of treating a patient having an autoimmune diseases manifesting activated T-cells or activated B-cells or both by providing a Fas ligand therapeutic agent, which can include a polypeptide, polynucleotide encoding a polypeptide, a peptide, a peptoid, or an organic small molecule agonist, and by administering an effective amount of the Fas ligand therapeutic agent to a mammal having an autoimmune disease.

Another aspect of the invention is a composition comprising a gene delivery vehicle capable of expressing a polynucleotide sequence encoding a Fas ligand polypeptide.

Additionally, another aspect of the invention is a therapeutic agent for treating an autoimmune disease where the therapeutic agent is derived from a Fas ligand and has also a pharmaceutically acceptable carrier for administering the agent to a mammal having the autoimmune disease.

Another aspect of the invention is a Fas ligand polypeptide capable of remaining on a cell membrane longer than native Fas ligand.

Another aspect of the invention is a polynucleotide encoding said Fas ligand polypeptide capable of remaining on a cell membrane longer than native Fas ligand.

Another aspect of the invention is a host cell transformed with a polynucleotide sequence encoding a Fas ligand polypeptide that is either a full length Fas ligand polypeptide, a biologically active portion of Fas ligand polypeptide, a membrane-bound Fas ligand polypeptide, or a sequence encoding a soluble Fas ligand polypeptide.

Another aspect of the invention is a method for reducing a population of activated T-cells or activated B-cells that comprises transforming a cell to express a non-cleavable Fas ligand polypeptide that remains membrane-bound thereto, wherein the transformed cell also bears a second ligand recognized by the activated T-cells or activated B-cells, and re-introducing this transformed cell into the population of activated T-cells or activated B-cells.

DETAILED DESCRIPTION OF THE INVENTION

The invention described herein draws on previously published work and pending patent applications. By way of example, such work consists of scientific papers, patents or pending patent applications. All such published work and pending patent applications cited herein are hereby expressly incorporated by reference in full.

Definitions

"Fas ligand" refers to a substance provided with an activity to induce apoptosis of a Fas-antigen presenting cell by binding to the Fas antigen expressed on the surface of the cell. Apoptosis in such a cell is believed to result when Fas ligand binds Fas expressed on a cell surface. Fas ligand can be membrane bound or soluble. Both the DNA (SEQ ID NO: 11) and the amino acid (SEQ ID NO: 12) sequences for human Fas ligand are well known in the art and are disclosed in EP 675 200, Suda et al, *Cell*, 75: 1169–1178 (1993), Takahashi et al, *Int'l Immunol.* 6(10):1567–74 (1994), and Nagata, *Adv. in Immun.* 57: 129–144 (1994), all incorporated by reference in full. Fas ligand is a member of the membrane-type tumor necrosis factor (TNF) cytokine family. Many of the members of this family are associated with apoptosis activity. The activity of Fas ligand includes the ability to bind Fas and induce apoptosis in cells that express Fas. The membrane-bound human Fas ligand is converted to a soluble form by the action of a matrix metalloproteinase-like enzyme. Sera from healthy humans do not contain a detectable level of soluble Fas ligand, as described in Tanaka et al, *Nature Medicine* 2(3): 317–22 (1996). Mammalian expression of Fas ligand in healthy individuals indicates low levels of expression in lymphoid organs (thymus, lymph node, spleen), lung and small intestine, demonstrating Fas ligand involvement in the general immune system and mucosal immunity. The testis expresses a splice variant of Fas ligand that is shorter than the T-cell Fas ligand. Activation of the splenocytes with the T-cell activators such as PMA and ionomycin, Con A, anti-CD3, or IL-2 alone, induce Fas ligand expression. CD8 splenocytes express Fas ligand more abundantly than CD4 splenocytes upon activation, as described in Suda et al, *J. of Immunol.* 154(8):3806–13 (1995). Further, functional soluble Fas ligand is expressed in activated lymphocytes as a 40 kDa protein, and is believed to exist in humans as a trimer in the soluble form, as described in Tanaka et al, *EMBO J.* 14(6):1129–35 (1995).

A "Fas ligand polypeptide" embodies variants, derivatives, analogues, fragments, chimeras and mutants of the native sequence of Fas ligand. The polypeptides are encoded by recombinantly produced polynucleotides sequences designed to encode the specific Fas ligand polypeptide intended for expression in a host cell.

A "Fas ligand therapeutic agent" includes molecules derived from Fas ligand native polynucleotide or polypeptide sequence, and variants, mutants, analogues, chimeras, and fragments of such Fas ligand polynucleotide or polypeptide. Polynucleotide Fas ligand therapeutic agents are generally sequences encoding a Fas ligand polypeptide that can be recombinantly expressed in a host cell. Additionally, a Fas ligand therapeutic agent can be a small molecule agonist of Fas ligand activity. Other Fas ligand therapeutic agents may include modulators of Fas ligand activity that effect Fas ligand and cause a therapeutic effect associated with Fas ligand activity or its absence. A modulator of Fas ligand can be, for example, a polynucleotide, a polypeptide, or a small molecule.

"Fas antigen" or "Fas" refers to a membrane-associated polypeptide expressed on an antigen presenting cell, capable of binding Fas ligand and inducing apoptosis, or cell death, of the cell bearing Fas. Fas antigen is described in Itoh et al, *Cell* 66:233–243 (1991), and Nagata, *Adv. in Immun.* 57: 129–144 (1994), both incorporated by reference in full. Activated human T and B cells, for example, APCs, abundantly express Fas as described in Trauth et al, *Science* 245: 301–305 (1989). Fas is a cell surface receptor that belong to the tumor necrosis factor (TNF)/nerve growth factor receptor family. Fas can transduce an apoptotic signal through the death domain in the cytoplasmic region.

The term "diagnostic agent," as used herein, refers to any agent that contributes to one or more of the diagnostic uses of the invention. These diagnostic uses include methods for determining the presence of Fas presenting cells. The diagnostic agents include the following: DNA encoding a Fas ligand mutein (preferably a mutein which is substantially non-cleavable from the surface of the cell in which it is expressed), the non-cleavable Fas ligand mutein (which is capable of specifically binding to Fas), and cells or the membranes of cells having the non-cleavable Fas ligand mutein surface bound thereto.

A "therapeutic agent" as used herein can be any agent that accomplishes or contributes to the accomplishment of one or more of the therapeutic elements of the invention. For example, where the therapeutic agent is a polynucleotide designed to express a Fas ligand polypeptide, that agent is a polynucleotide that can be administered to and expressed in a cell in the mammal. Thus, the active form of the agent will initially be the expressed polypeptide. A Fas ligand therapeutic agent is a therapeutic agent with the bioactivity of Fas ligand or a therapeutic agent derived from native Fas ligand, such as a polynucleotide encoding a Fas ligand polypeptide capable of remaining membrane-bound longer than native Fas ligand. A therapeutic agent achieves a therapeutic goal, alone or in combination with other agents, for example, the use of other known treatments for a particular autoimmunity used in conjunction with administration of Fas ligand, or a gene delivery vehicle capable of facilitating expression of Fas ligand in the mammal. The therapeutic agents including for example agonists of Fas ligand or drugs developed for other purposes can be, for example, a small organic molecule, a peptide, a peptoid (defined below), a polynucleotide encoding a Fas ligand polypeptide, a polypeptide Fas ligand therapeutic agent, or a transformed cell expressing a Fas ligand mutant that is surface bound thereto and substantially non-cleavable therefrom.

A "combination therapeutic agent" is a therapeutic composition having several components or agents that produce their separate effects when administered together, and may produce a synergistic effect when administered together to treat a disease. Preferably, the separate effects of the combination therapeutic agent combine to result in a larger therapeutic effect, for example recovery from an autoimmune disease and long term survival. An example of separate effects resulting from administration of a combination therapeutic agent is the combination of such effects as short-term, or long-term remission, or decrease of an autoimmune response to a particular type of cell in the patient. An example of a combination therapeutic agent of this invention would be administration of a gene delivery vehicle including a polynucleotide encoding a mutant or native Fas ligand and HSV thymidine kinase. Alternatively, two gene delivery vectors can be used, one expressing Fas ligand and one encoding HSV thymidine kinase. Also by example, IFNγ, or a gene delivery vehicle expressing IFNγ, can be administered to upregulate Fas expression in anticipation of an administration of Fas ligand for inducing apoptosis in the Fas expressing cells. The various therapeutic agents can be administered in the same pharmaceutically acceptable carrier at the same time, followed, for example, by repeated administration of one or all of the individual agents as needed to make the therapy efficacious.

A "gene delivery vehicle" refers to a component that facilitates delivery to a cell of a coding sequence for expression of a polypeptide in the cell. The cell can be inside the mammal, as in in vivo gene therapy, or can be removed from the mammal for transfection and returned to the mammal for expression of the polypeptide as in ex vivo gene therapy. The gene delivery vehicle can be any component or vehicle capable of accomplishing the delivery of a gene to a cell, for example, a liposome, a particle, or a vector. A gene delivery vehicle is a recombinant vehicle, such as a recombinant viral vector, a nucleic acid vector (such as plasmid), a naked nucleic acid molecule such as genes, a nucleic acid molecule complexed to a polycationic molecule capable of neutralizing the negative charge on the nucleic acid molecule and condensing the nucleic acid molecule into a compact molecule, a nucleic acid associated with a liposome (U.S. Pat. No. 5,166,320, issued Nov. 24, 1992; and Wang, et al., *PNAS* 84:7851, 1987), and a bacterium. Gene delivery vehicles include certain eukaryotic cells such as a producer cell, that are capable of delivering a nucleic acid molecule having one or more desirable properties to host cells in an organism. As discussed further below, the desirable properties include the ability to express a desired substance, such as, for example, a protein, enzyme, or antibody, and/or the ability to provide a biological activity, which is where the nucleic acid molecule carried by the gene delivery vehicle is itself the active agent without requiring the expression of a desired substance. One example of such biological activity is gene therapy where the delivered nucleic acid molecule incorporates into a specified gene so as to inactivate the gene and "turn off" the product the gene was making. Gene delivery vehicle refers to an assembly which is capable of directing the expression of the sequence(s) or gene(s) of interest. The gene delivery vehicle generally includes promoter elements and may include a signal that directs polyadenylation. In addition, the gene delivery vehicle includes a sequence which, when transcribed, is operably linked to the sequence(s) or gene(s) of interest and acts as a translation initiation sequence. The gene delivery vehicle may also include a selectable marker such as Neo, $SV^2$ Neo, TK, hygromycin, phleomycin, histidinol, or DHFR, as well as one or more restriction sites and a translation termination sequence. Gene delivery vehicles as used within the present invention refers to recombinant vehicles, such as viral vectors (Jolly, *Cancer Gen. Therapy* 1:51–64, 1994), nucleic acid vectors, naked DNA, liposomal DNA, cosmids, bacteria, and certain eukaryotic cells (including producer cells; see U.S. Ser. No. 08/240,030 and U.S. Ser. No. 07/800,921), that are capable of eliciting an immune response within an animal.

"Biologically active" refers to a molecule that retains a specific activity. A biologically active Fas ligand polypeptide, for example, retains the ability to bind Fas antigen on a cell surface, and activate the apoptotic pathway leading to apoptosis of the Fas antigen expressing cell.

"B-cells" or "B lymphocytes" refer to lymphocytes that mature in the bone marrow and are precursors of antibodysecreting plasma cells, as described in Kuby, IMMUNOLOGY, (W.H. Freeman, NY 1992). B-cells can be activated by antigen to become antigen presenting cells (APCs) and expresses Fas upon such activation. An activated B-cell undergoes apoptosis in the presence of either soluble or cell membrane associated Fas ligand.

"T-cells" or "T lymphocytes" refer to lymphocytes that mature in the thymus, where they undergo differentiation. T-cell possess a rearranged T-cell receptor. A "CD4 T-cell" refers to a T-cell that possesses a cell membrane molecule identifies the T lymphocyte or T-cell as a subset of lymphocytes. CD4 is a cell surface glycoprotein found on a subset of the T-cells that recognize antigenic peptides complexed to class II MHC, as described in Kuby, IMMUNOLOGY, (W.H. Freeman & Co., NY 1992). CD4 T-cells can express cytotoxic activity. While activation of CD4 CTLs (cytotoxic T-lymphocytes) is MHC-class II-restricted, the target cell killing activity is unrestricted and non-specific for antigen. CD4 CTLs preferentially lyse their targets via Fas-Fas ligand interaction, which is a different mechanism than that used by CD8 T-cells which used granule exocytosis. Although CD8 T-cells can also express the Fas ligand, their lytic activity through interaction with Fas is of less importance.

A "nucleic acid molecule" or a "polynucleotide," as used herein, refers to either RNA or DNA molecule that encodes a specific amino acid sequence or its complementary strand. A "coding sequence" as used herein, refers to either RNA or DNA that encodes a specific amino acid sequence or its complementary strand. A polynucleotide may include, for example, an antisense oligonucleotide, or a ribozyme, and may also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degradation. A polynucleotide, and can be generated, for example, by polymerase chain reaction (PCR) amplification, or recombinant expression of complementary DNA or RNA, or by chemical synthesis.

The term "an expression control sequence" or a "regulatory sequence" refers to a sequence that is conventionally used to effect expression of a gene that encodes a polypeptide and include one or more components that affect expression, including transcription and translation signals. The expression control sequence that is appropriate for expression of the present polypeptides differs depending upon the host system in which the polypeptide is to be expressed.

Any "polypeptide" of the invention, including a Fas ligand polypeptide, includes any part of the Fas ligand protein including the mature protein, and further include truncations, variants, alleles, analogs and derivatives thereof. Variants can be spliced variants expressed from the same gene as the related protein. Unless specifically mentioned otherwise, such a polypeptide possesses one or more of the bioactivities of the protein, including for example binding activity to a specific partner. This term is not limited to a specific length of the product of the gene. Thus, polypeptides that are identical or contain at least 60%, preferably 70%, more preferably 80%, and most preferably 90% homology to the target protein or the mature protein, wherever derived, from human or nonhuman sources are included within this definition of a polypeptide. Also included, therefore, are alleles and variants of the product of the gene that contain amino acid substitutions, deletions, or insertions. The amino acid substitutions can be conservative amino acid substitutions or substitutions to eliminate nonessential amino acid residues such as to alter a glycosylation site, a phosphorylation site, an acetylation site, or to alter the folding pattern by altering the position of the cysteine residue that is not necessary for function. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Cys/Thr and Phe/Trp/Tyr. Analogs include peptides having one or more peptide mimics, also known as peptoids, that possess the target protein-like activity. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "polypeptide" also does not exclude post-expression modifications of the polypeptide, for example, glycosylations, acetylations, phosphorylations, myristoylations and the like.

The term "naked DNA" refers to polynucleotide DNA for administration to a mammal for expression in the mammal. The polynucleotide can be, for example, a coding sequence, and the polynucleotide DNA can be directly or indirectly connected to an expression control sequence that can facilitate the expression of the coding sequence once the DNA is inside a cell. The direct or indirect connection is equivalent from the perspective of facilitating the expression of the DNA in the mammal's cells, and merely allows the possibility of the inclusion of other sequences between the regulatory region and the coding sequence that may facilitate the expression further, or may merely act a linker or spacer to facilitate connecting the two polynucleotide regions together to form a nonviral vector.

"Vector" refers to an assembly which is capable of directing the expression of the sequence(s) or gene(s) of interest. The vector must include transcriptional promoter/enhancer or locus defining element(s), or other elements which control gene expression by other means such as alternate splicing, nuclear RNA export, post-translational modification of messenger, or post-transcriptional modification of protein. In addition, the vector must include a sequence which, when transcribed, is operably linked to the sequence(s) or gene(s) of interest and acts as a translation initiation sequence. Optionally, the vector may also include a signal which directs polyadenylation, a selectable marker such as Neo, TK, hygromycin, phleomycin, histidinol, or DHFR, as well as one or more restriction sites and a translation termination sequence. In addition, if the vector is placed into a retrovirus, the vector must include a packaging signal, long terminal repeats (LTRs), and positive and negative strand primer binding sites appropriate to the retrovirus used (if these are not already present).

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEPCK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, a or b globin promoters, T-cell receptor promoter, or the osteocalcin promoter.

"Event-specific promoter" refers to transcriptional promoter/enhancer or locus defining elements, or other elements which control gene expression as discussed above, whose transcriptional activity is altered upon response to cellular stimuli. Representative examples of such event-specific promoters include thymidine kinase or thymidilate synthase promoters, α or β interferon promoters and promoters that respond to the presence of hormones (either natural, synthetic or from other nonhost organisms, e.g., insect hormones).

The term "fusion protein" or "fusion polypeptide" refers to the recombinant expression of more than one heterologous coding sequence in a vector or contiguous connection such that expression of the polypeptide in the vector results in expression of one polypeptide that includes more than one protein or portion of more than one protein. Most optimally, the fusion protein retains the biological activity of at least one of the polypeptide units from which it is built, and preferably, the fusion protein generates a synergistic improved biological activity by combining the portion of the separate proteins to form a single polypeptide. A fusion protein can also be created with a polypeptide that has function and a peptide or polypeptide that has no function when expressed, but which serves a purpose for the expression of the polypeptide with activity. Examples of fusion proteins useful for the invention include any Fas ligand fusion polypeptide genetically engineered to some advantage for the therapy. The term "chimera" or "chimeric protein" is equivalent to fusion protein or fusion polypeptide. A "chimeric molecule" can be a fusion polypeptide, or a polynucleotide fusion molecule encoding a fusion polypeptide. Thus, for example, a fusion protein can have an extracellular receptor binding domain of Fas ligand, and a transmembrane proximal and transmembrane domain of another protein, for example, a protein in the same family as Fas ligand, for example, TNF or CD30 ligand. The chimera can be constructed from ligated DNA coding sequences and expressed in a cell system, or administered in a vector for expression in vivo in an animal. For example, a chimera or fusion protein including a membrane bound Fas ligand can be administered in a gene therapy protocol in vivo or ex vivo. The chimeric polypeptide can be, for example, a fusion polypeptide comprising a Fas binding portion of Fas ligand fused to another transmembrane portion incapable of being cleaved from the membrane. The chimeric polypeptide can also be a fusion polypeptide of a Fas binding portion of Fas ligand fused to a synthetically derived sequence of amino acids that provide a fusion polypeptide incapable of being cleaved from the cell membrane.

The phrase "sequence encoding a membrane-bound Fas ligand" is meant to include a polynucleotide sequence encoding a Fas ligand mutein or a Fas ligand chimera molecule, the polynucleotide comprising a first DNA sequence encoding the Fas binding domain of Fas ligand linked to a second DNA sequence encoding the intracellular (and transmembrane) region of Fas ligand or a membrane bound receptor. For example, a membrane-bound Fas ligand can include a fusion protein having a Fas-binding domain and a polypeptide sequence of another transmembrane protein including replacement of the Fas ligand cleavage site, or a sequence that is not cleaved from the cell membrane. A fusion protein that makes up a membrane-bound Fas ligand can also be, for example, a Fas binding domain of Fas ligand polypeptide, and a synthetic sequence of amino acids such that the proximal extracellular portion of the fusion cannot be cleaved from the cell membrane, and such that the sequence of amino acids includes sufficient hydrophobicity for a transmembrane sequence, and such that the sequence of amino acids proximal intracellular is also appropriately configured with charge for constituting a fusion polypeptide capable of expression on but not cleavage from the cell membrane. For example a membrane-bound Fas ligand can include a chimera that has an extracellular and Fas-binding portion of the Fas ligand, an uncleavage domain and transmembrane portion of another protein of the same family as Fas ligand, and a cytoplasmic portion of the same or yet another protein in the same family as Fas ligand. Thus, for example, a sequence encoding a membrane-bound Fas ligand includes a polynucleotide sequence encoding an extracellular and Fas-binding portion of the Fas ligand ligated to a polynucleotide sequence encoding the intracellular and transmembrane domains of a member of the TNF receptor family. In addition to the Fas ligand chimeras being made with Fas ligand and portions of other members of the TNF superfamily, Fas ligand chimeras that enable Fas ligand to remain membrane-bound when expressed in cells can also be made of Fas ligand and portions of any other transmembrane protein such that cleavage of the Fas ligand from the membrane is prevented and the Fas ligand polypeptide remains membrane bound.

A "patient" can be any treatable living organism, including but not limited to a eukaryote or a prokaryote. The patient eukaryote can be, for example, a vertebrate or an invertebrate. Thus, for example, the patient can be a fish, a bird, a worm, an insect, a mammal, a reptile, an amphibian, a fungi, or a plant, preferably a mammal. The mammal can be, for example a human.

General Methods of Making And Using a Fas Ligand Therapeutic Agent And/Or Diagnostic Agent In one aspect, the present invention includes a method for treating an autoimmune disease manifesting activated T-cells or activated B-cells or both by providing a Fas ligand therapeutic agent, and administering an effective amount of the Fas ligand therapeutic agent to a mammal having an autoimmune disease. An "autoimmune disease", "autoimmune disease" and "autoimmunity" all refer to a disorder characterized by autoimmunity in the mammal which is the response of an immune system against self components. An autoimmune response can develop into a condition manifesting clinical symptoms. Although strictly speaking transplantation rejection is not an autoimmune reaction, where patient condition prescribes surgery to replace or graft cells, tissue or an organ, the body receiving the allograft can react immunologically against the foreign graft. "Transplantation rejection" occurs when during an allograft of cells, tissue, or an organ, from one member of a species to another, an immune response in the recipient results, sufficient to reject the transplanted cells, tissue or organ.

Examples of "autoimmune diseases" that can be treated by the method and therapeutic agent of the invention include multiple sclerosis, Hashimoto's thyroiditis, systemic lupus erythematosus (SLE), Goodpasture's syndrome, Pemphigus, receptor autoimmunity, autoimmune hemolytic anemia, autoimmune thrombocytopenic purpura, osteoarthritis, rheumatoid arthritis, schleroderma with anticollagen antibodies, mixed connective tissue disease, polymyositis, pernicious anemia, idiopathic Addison's disease, spontaneous infertility, glomerulonephritis, bullous pemphigoid, adrenergic drug resistance, chronic active hepatitis, primary biliary cirrhosis, autoimmune-based endocrine gland failure, vitiligo, vasculitis, post-myocardial infarction, cardiotomy syndrome, urticaria, atopic dermatitis, autoimmune-based asthma, autoimmune-based inflammatory reactions, granulomatous disorders, alkylizing spondylitis, poststreptococcal glomerulonephritis, autoimmune hemolytic anemia, encephalitis, autoimmune reaction secondary to lymphoma, degenerative disorders, and atrophic disorders. Autoimmune diseases manifesting receptor autoimmunity include, for example, Grave's disease, myasthenia gravis, and insulin resistance. Autoimmune diseases of adrenergic drug resistance include, for example, asthma and cystic fibrosis.

Other autoimmune diseases appropriate for the invention include, for example those for which an animal model exists, including for example, Sjogren's syndrome (autoimmune dacryodentis or immune-mediated sialadenitis), autoimmune myocarditis, primary biliary cirrhosis (PBC), inflammatory heart disease, mercury-induced renal autoimmunity, insulin dependent diabetes mellitus (type I diabetes or IDD), post-thymectomy autoimmunity, a central nervous system (CNS) demyelination disorder, CNS lupus, narcolepsy, a immune-mediated PNS disorder, osteoarthritis, rheumatoid arthritis, uveitis, medullary cystic fibrosis, autoimmune hemolytic disease, autoimmune vasculitis, ovarian autoimmune disease, and human scheroderma. An autoimmune disease characterized by a central nervous system (CNS) demyelination disorder can be, for example, multiple sclerosis (MS). A peripheral nervous system (PNS) autoimmune disease can be, for example, Guillain-Barre syndrome (GBS).

The Fas ligand therapeutic agent can be a polypeptide, a polynucleotide, a small organic molecule, a peptide or a peptoid. The Fas ligand therapeutic agent can be a Fas ligand polypeptide, a polynucleotide encoding a Fas ligand polypeptide, a fusion polypeptide comprising a portion of native Fas ligand polypeptide, a polynucleotide encoding a fusion polypeptide comprising a portion of native Fas ligand polypeptide, a biologically active peptide derivative of Fas ligand polypeptide, a biologically active peptoid derived from Fas ligand polypeptide, or a small organic molecule agonist of Fas ligand activity. The Fas ligand polypeptide can be a biologically active Fas ligand polypeptide such as a Fas ligand polypeptide variant, a Fas ligand polypeptide derivative, a modified Fas ligand polypeptide, or a truncated Fas ligand polypeptide. The polynucleotide encoding a Fas ligand polypeptide can be a polynucleotide sequence encoding full length Fas ligand polypeptide, a sequence encoding a biologically active portion of Fas ligand polypeptide, a sequence encoding a biologically active peptide derived from Fas ligand polypeptide, a sequence encoding membrane-bound Fas ligand polypeptide, or a sequence encoding a soluble Fas ligand polypeptide. Another embodiment of the invention is a composition having a gene delivery vehicle capable of expressing a polynucleotide sequence encoding a Fas ligand polypeptide.

The Fas ligand polypeptide of the compositions of the invention include a membrane-bound Fas ligand polypeptide. In a preferred embodiment, the Fas ligand polypeptide is a recombinant Fas ligand that is capable of remaining on a cell membrane longer than native Fas ligand, more preferably, the membrane bound recombinant Fas ligand is substantially non-cleavable from the surface of the expressing cell. The invention also includes, therefore, a host cell, preferably a human host cell, transformed with a polynucleotide sequence encoding a Fas ligand polypeptide selected from the group consisting of a full length Fas ligand polypeptide, a biologically active portion of Fas ligand polypeptide, a membrane-bound Fas ligand polypeptide, and a sequence encoding a soluble Fas ligand polypeptide. Preferably, the host cell is a T-cell. Thus, in its therapeutic embodiment, the invention is also directed to a method of reducing a population of activated T-cells or activated B-cells by transforming a host cell with a Fas ligand polypeptide that remains membrane-bound, wherein the host cell also bears another ligand recognized by the activated T-cells or activated B-cells, and re-introducing the transformed cell into the population of activated T-cells or activated B-cells. This method is particularly suited to treatment of an autoimmune disease (which is mediated by activated T cells or B cells) or transplantation rejection. In this method, the other ligand is natively expressed by the cell, or a polynucleotide encoding the other ligand is used to transform the host cell for expression therein. Examples of some of the autoimmune diseases treatable by the method of the present invention include rheumatoid arthritis (RA), primary biliary cirrhosis (PBS), systemic lupus erythmatosis (SLE), and idiopathic thrombocytopenic purpura (ITP).

When used in the therapeutic embodiment, the host cell is more preferably an allogeneic host cell, and most preferably a syngeneic host cell. Transduction or transformation of the host cell is performed in vivo or ex vivo, more preferably ex vivo using techniques and vectors that are well known in the art. See U.S. Pat. No. 5,399.346 (Anderson) and U.S. Ser. No. 08/463,122, filed Jun. 5, 1995, now allowed, both of which are hereby expressly incorporated herein by reference for their disclosures of said techniques and vectors.

The same host cell having the non-cleavable (or substantially non-cleavable) Fas-ligand on its surface is capable of being used in a diagnostic embodiment to detect activated T cell or B cells having Fas (antigen) expressed on their surface. In particular, the diagnostic method of this embodiment comprises:

a) providing a transformed host cell having a recombinant Fas ligand surface bound thereto, said surface bound Fas ligand mutein being resistant to cleavage;
  b) contacting said transformed cell with a sample containing an excess of cells suspected of having surface bound Fas thereon to obtain a cell mixture;
  c) allowing said cell bound Fas to bind to said cell bound recombinant Fas ligand; and
  d) observing said cell mixture for rosette formation or clumping, whereby rosette formation or clumping indicates the presence of cells having Fas thereon in said sample.

The cells to be tested in the present inventory are typically centrifuged to separate them from any soluble interfering substances. The centrifuged cells are resuspended in any of a variety of balanced salt solutions, such including Hank's, Earle's saline, or Dulbecco's buffered saline. To obtain rosette formation, the cells suspected of having Fas expressed on their surface are provided in excess, relative to the RFL cell, typically 25:1, preferably 40:1, more preferably 100:1. See Smith et al. "A Modified Assay For The Detection Of Human Adult Active T Rosette Forming Lymphocytes," *J. Immunol. Methods*, 8:175–184 (1975); Fandenberg et al., "T-rosette-Forming Cells: Cellular Immunity and Cancer," *N. Eng. J. Of Med.*, 292:465–475 (1975); and Kerman et al., "Active T Rosette Forming Cells in the Peripheral Blood of Cancer Patients," *Cancer Res.*, 36:3274–3278 (1976).

As the above cited references reflect, various methods for observing rosette formation are well known to the art.

When the above described method of detecting activated T cells and B cells is performed with human T cell and B cells, the transformed host cell is preferably a human host cell.

Ultimately, when cell bound Fas binds to a Fas ligand, including the membrane bound Fas ligand of the present invention, the cell with the Fas surface bound thereon goes into apoptosis and dies. Thus, the present invention is also directed to a method for reducing the population of activated T cells and/or B cells, the method comprising the steps of:

a) contacting a population of activated T cells and/or B cells with a transformed cell expressing a recombinant Fas ligand that is surface bound thereon, said activated T cells and/or B cells having a cell membrane with Fas expressed thereon, said Fas ligand on said cell binding to said Fas on said activated T cells and/or B cells, and inducing apoptosis in said activated T cells and or B cells, whereby said population is reduced.

The term "membrane bound Fas ligand" as used in the present invention, not only includes muteins of Fas ligand that are non-cleavable (and thus remain membrane bound), but also a chimera or a fusion protein of Pas ligand.

The present invention is also directed to a chimera or fusion protein for providing a membrane bound Fas ligand that induces apoptosis in activated T-cells and B-cells, for the purpose of a treatment of certain autoimmune diseases is that Fas ligand binds to Fas and induces apoptosis of Fas expressing cells. It has been shown that Fas ligand is cleaved from the cell surface to produce a soluble form of Fas ligand. The goal of construction of a chimera or fusion protein including a portion of the Fas ligand sequence is to restrict Fas ligand expression to the cell surface to protecting the expressing cell, tissue or organ from CTL (cytotoxic T-cell lymphocyte) mediated killing. Because such non cleavable receptor proteins TNF and CD30 ligand and other ligands of the same superfamily are also type II transmembrane proteins they are suited to forming a chimera with Fas ligand that allows Fas ligand to retain a similar transmembrane and cytoplasmic component as native Fas ligand. However, the advantage of using, for example, TNF for the transmembrane and cytoplasmic portion is that the site of cleavage on TNF is well defined, and the TNF portion of the fusion protein can be mutated to be substantially noncleavable. Fusions can be made of the extracellular domain of Fas ligand, retaining at least the portion of Fas ligand that binds to Fas, and uncleavable transmembrane and intracellular domain of, for example a modified TNF sequence, or other polypeptide, for example, uncleavable transmembrane and intracellular domains of other members of that ligand superfamily. Thus, the chimera as described binds Fas and induces apoptosis in Fas-expressing cells, but is not cleaved from the surface of the cell in which the chimera is expressed. The Fas ligand chimera can also be constructed using portions of any other transmembrane protein for the purpose of making the Fas ligand extracellular portion of the chimera that is capable of binding Fas and inducing apoptosis in Fas expressing cells but that remains membrane-bound. Examples of such transmembrane proteins from which can be derived a polypeptide sequence appropriate for constructing a Fas ligand fusion protein having the ability to bind Fas but also the ability to remain membrane-bound, include such membrane-bound transmembrane proteins as membrane-bound antibodies, viral antigens that remain membrane-bound, or proximally extracellular/transmembrane/and intracellular portions of other known transmembrane proteins. Additionally, any operable combination of protein sequence and synthetically designed sequence, for example a sequence of hydrophobic amino acids to anchor the fusion protein in the membrane can be figured into the design of a Fas ligand fusion polypeptide.

Chimeric molecules or fusion proteins can be created that express a membrane-bound Fas ligand chimera. For example, the region of pro-Fas ligand (SEQ ID NO: 12) extending 129 residues from M1 to Q130 of the pro-protein (i.e., SEQ ID NO: 2) can be replaced by another polypeptide sequence that provides a fusion protein capable of expression on the cell membrane and capable of binding to Fas, but also capable of remaining on the cell membrane longer than native Fas ligand. The polypeptide sequence that is used in the fusion with the Fas binding portion of Fas ligand can be another transmembrane protein, preferably one that is not normally cleaved from the cell membrane, or a polypeptide sequence that includes a synthetically assimilated sequence that provides for the proper amino acid content for the proximal extracellular domain, the transmembrane domain, and the proximal intracellular domain.

For example, the extracellular sequence of Fas ligand from I131 to L281, and which binds Fas, can be retained as the Fas binding portion of the fusion protein. The proximal extracellular domain (of the fusion polypeptide) corresponding to about 14 amino acids (in the native Fas ligand protein) can be a multiple proline sequence, or a sequence having mostly proline amino acids or amino acids forming a sequence that is not normally cleaved from the cell membrane by a protease or convertase. The sequence of the transmembrane portion of the fusion polypeptide can be of hydrophobic amino acids having nonpolar side chains, including for example the amino acids alanine, valine, leucine, isoleucine, proline, phenylalanine, tryptophan, and methionine. The sequence of the fusion polypeptide of amino acids proximally intracellular can be amino acids with charged side chains including, for example, aspartic acid and glutamic acid which are negatively charged at pH 6.0, and lysine, arginine, and histidine which are positively charged at pH 6.0. The remainder of the fusion polypeptide can be a sequence appropriate for an intracellular portion of a transmembrane polypeptide, and might preferably be a sequence of Fas ligand or of a member of the TNF family of ligands so that any effects that the intracellular portion of the molecule may have on the biological activity desired from the Fas ligand derived polypeptide fusion might be retained.

The Fas ligand fusion polypeptide can also be made up of a Fas ligand extracellular portion including the portion of Fas ligand that binds Fas and promotes signaling, and the transmembrane and intracellular portion of another member of the same family (the tumor necrosis factor family). The fusion protein construct is especially effective where the intracellular region of Fas ligand and the Fas ligand cleavage site is replaced with an uncleavable domain, such as, for example, the intracellular and transmembrane domains one of the members of the TNF receptor family of proteins, such as TNFR, CD30 or CD40. The result is a membrane-bound polypeptide having Fas ligand capable of binding Fas for activating apoptosis in Fas expressing cells. Such a chimera is well suited to a gene therapy administration by using a gene delivery vehicle, and can thus facilitate activating apoptosis in Fas expressing cells, such as, for example activated T-cells or activated B-cells involved to protect target cells/tissues/organs in the context of an autoimmune disease or transplant rejection. The DNA sequences for the various members of the TNF receptor family are well known in the art. In particular, the cloning of TNFR and CD40 is disclosed in the following references, each of which is hereby incorporated by reference: Schall, et al., "Molecular Cloning and Expression of a Receptor for Human Tomor Necrosis Factor," *Cell* 61:361–370 (1990); and Stamenkovic et al., "A B-lymphocyte Activation Molecule Related to the Nerve Growth Factor Receptor and Induced by Cytokines in Carcinomas," *EMBO J* 8(5):1403–1410 (1989).

Fusion proteins are constructed, for example, by replacing a fragment of Fas ligand with an uncleavable fragment from a cell surface receptor, for example CD30, CD40, or a TNFR, or even an uncleavable portion of another transmembrane protein. For example, substitution of the fragment of Fas ligand from L127 to R144 with a fragment of CD30 ligand from S83 to A100 or a fragment of CD40 ligand from E104 to Q121 results in a mutant or fusion protein Fas ligand with the replacement in the cleavage site that provides that the mutant remains membrane-bound.

Yet another variation is construction of a chimeric molecule of C-terminal from Fas ligand from I131 to L281 fused to the N-terminal CD30 ligand from M1 to L86 or the N-terminal of CD40 ligand from M1 to K107. The resulting chimera is membrane bound and uncleavable.

Using standard gene splicing techniques that are well known in the art, gene constructs are made that encode a chirneric Fas ligand polypeptide that is expressed in membrane bound form. In such constructs, approximately the first fourteen amino acid region of the extracellular region of the Fas ligand may be deleted or replaced. Deletion of the DNA coding for this region provides a Fas ligand molecule that is not be cleaved, as cleavage of native-sequence Fas ligand from the cell membrane is believed to occur within this region. Replacement of this coding region with the corresponding coding region of any transmembrane receptor protein that is not cleaved in that region, creates a DNA encoding a fusion protein that is also not susceptible to cleavage, and thus remains membrane-bound.

Alternatively, as described above, the Fas ligand can be the basis of a chimeric but non-cleavable starting with replacement of membrane bound Fas ligand, the portion of the extracellular region of Fas ligand believed to be the cleavage site for a protease that releases soluble Fas ligand, (preferably the first 14 amino acids of the extracellular region), and the remainder of the N-terminal region of the Fas ligand can be replaced with the corresponding sequence of CD30, or CD40, or other member of the TNF receptor family provided that the TNF receptor is not cleaved at the replaced sequence, or that the replaced sequence is altered to prevent cleavage. Finally, the Fas ligand sequence can be mutagenized at the region where the clipping of the membrane-bound molecule is believed to occur, to prevent or reduce the likelihood of cleavage, using standard mutagenesis techniques, such as taught by Gilman et al., Gene, 8:81 (1979) and Roberts et al., Nature, 328:731 (1987). The resulting Fas ligand mutant is also a cleavage resistant variant of the native Fas ligand, and thus, stays membrane bound longer when expressed in a host cell. The resulting membrane bound ligand when expressed in a transduced host cell protects cells/tissues/organ expressing Fas and eliminates side effects of soluble Fas ligand when cleaved off the membrane.

Also within the scope of this invention are Fas ligand deletion muteins which when expressed in a host cell become membrane bound Fas ligand agonists that are substantially non-cleavable. In one embodiment of the present invention, the Fas ligand deletion mutein is a deletion mutein of pro-Fas ligand that lacks a segment of 4 to 17 amino acid residues beginning at about residue position 127 of pro-Fas ligand (SEQ ID NO: 12). Preferably, the deletion mutein of pro-Fas ligand lacks a continuous segment of 10 to 17 amino acids begining at about residue 130 of pro-Fas ligand (SEQ ID NO: 12). More preferably, the Fas ligand deletion mutein has a deletion selected from the group consisting of 130→139, 130→140, 130→141, 130→142, 130→143, 130→144, 130→145, 130→146, 131→140, 131→141, 131→142, 131→143, 131→144, 131→145 and 131→146.

To make a membrane-bound uncleavable Fas ligand, DNA encoding four to seventeen residues from residue positions L127 to R144 of Fas ligand native sequence is deleted from a genomic or cDNA (SEQ ID NO: 11). Expression of this deletion mutein of Fas ligand produces a Fas ligand agonist that is substantially non-cleavable. The preparation of specific deletion muteins of Fas ligand are disclosed in the specification at Examples 5 and 6. In Example 5, a polynucleotide (SEQ ID NO: 1) encoding the first 129 amino acid residues (SEQ ID NO: 2) of Fas ligand was ligated to a second polynucleotide (SEQ ID NO: 3) encoding residues 143–282 of Fas ligand. The resulting polynucleotide (SEQ ID NO: 5) encoded the non-cleavable Fas ligand$_{130\rightarrow142}$ deletion mutein (SEQ ID NO: 6). In example 6, a polynucleotide (SEQ ID NO: 1) encoding the first 129 amino acid residues (SEQ ID NO: 2) of Fas ligand was ligated to a second polynucleotide (SEQ ID NO: 7) encoding residues 146–282 of Fas ligand. The resulting polynucleotide (SEQ ID NO: 9) encoded the non-cleavable Fas ligand$_{130\rightarrow145}$ deletion mutein (SEQ ID NO: 10).

A Fas ligand fusion protein having a Fas binding portion of amino acid residues R144 to L281, and a cell surface molecule binding portion can be constructed. For example, the cell surface molecule binding portion can be heparin, and the cell surface molecule to which it binds can be a glycosaminoglycan molecule. Such a polypeptide fusion protein, for example using heparin and Fas ligand, can be constructed as described in U.S. Ser. No. 07/608,539, filed Nov. 1, 1990, and U.S. Ser. No. 07/608,569, filed Nov. 2, 1990. This Fas ligand fusion polypeptide can be expressed and purified in any standard expression system suitable for producing sufficient quantities of the recombinant protein, and for any necessary post translational modifications. Once purified the polypeptide can be used, for example, to bathe the organ or tissue to be transplanted, before entry into the transplant recipient. The Fas ligand polypeptide binds at its heparin portion, cell surfaces on the external cells of the organ or tissue. When the organ, so treated, is placed in the patient, any activated T-cells attempting to generate an immune rejection to the foreign organ or tissue encounters Fas ligand coated cells. Upon binding to Fas of the Fas ligand portion coating the cells, the activated T-cells expressing Fas undergoes apoptosis, thus reducing the immune rejection of the organ or tissue.

In all cases of the above described fusion polypeptides, and all obvious variations and permutations of these fusion polypeptides, construction can be facilitated by constructing a polynucleotide chimera capable of expressing the desired polypeptide fusion. Any mutations and deletions in such polynucleotide constructs can be conducted using standard mutagenesis (such as taught by Gilman et al., Gene, 8:81 (1979) and Roberts et al., Nature, 328:731 (1987)) and restriction digest cleavage and ligation in standard plasmids or vectors. In many cases, the fusion polypeptide can be made by starting with DNA encoding native Fas ligand and DNA encoding another transmembrane protein. Addition of synthetic sequences can also be accomplished by standard techniques. Any member of the TNF family of ligands, and in some cases any transmembrane protein, may be suitable for arranging a chimera or mutant along the lines described in order that a Fas ligand signaling polypeptide is created that remains membrane bound for the purpose of binding and signaling through Fas on another cell, for example an activated T-cell or B-cell.

In the case of polynucleotides encoding Fas ligand polypeptides for expression in cells to target activated T-cells or B-cells or other Fas expressing cells harmful to an organism, the polynucleotide constructs, once designed, for example, as described herein, can be constructed by standard recombinant DNA technology and manipulation. For example, polynucleotide constructs having deletions, mutations, substitutions, fusions, and which otherwise encode polypeptide variants, derivatives, mutants, analogues, or chimeras of Fas ligand can be constructed by conventional techniques of molecular biology, microbiology, and recombinant DNA technology that are within the skill of the art. The Fas ligand polynucleotide can be placed into a vector which directs its expression.

Such techniques for polynucleotide and polypeptide construction and expression are explained fully in the literature, for example in Sambrook, et al. MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), HANDBOOK OF EXPERIMENTAL IMMUNOLOGY, VOLUMES I–IV (D. M. Weir and C. C. Blackwell eds 1986); and VACCINES (R. W. Ellis, ed., 1992, Butterworth-Heinemann, London). Standard abbreviations for nucleotides and amino acids are used in this specification. All publications, patents, and patent applications cited herein are incorporated by reference. Further, sequences that encode the above-described genes may also be synthesized, for example, on an Applied Biosystems Inc. DNA synthesizer (e.g., ABI DNA synthesizer model 392 (Foster City, Calif.)). Additionally, the polynucleotides can be constructed and cloned as described in PCR PROTOCOLS, Cold Spring Harbor, N.Y. 1991. The desired gene can also be isolated from cells and tissues containing the gene, using phenol extraction, PCR of cDNA, or genomic DNA. The gene of interest can also be produced synthetically, rather than cloned, as described in Edge, $Nature$ 292: 756 (1981), Nambair et al, $Science$ 223: 1299 (1984), and Jay et al, $J. Biol. Chem.$ 259: 6311 (1984). Additionally, variations of any polynucleotide or polypeptide can be made by conventional techniques, including PCR or site-directed mutagenesis (such as taught by Gilman et al., Gene, 8:81 (1979) and Roberts et al., Nature, 328:731 (1987)). The DNA construct so synthesized can be ligated to an expression plasmid containing an appropriate promoter for expression in a desired host expression system. The host system can be in vitro, in vivo or ex vivo. In all cases, assay for whether the Fas ligand polypeptide (expressed in vivo, ex vivo or in vitro) is functional in terms of binding Fas when expressed on a cell, and whether, more specifically, any of the Fas ligand fusion polypeptides are capable of remaining membrane bound longer than native Fas ligand, can be determined by standard assays, for example, as described herein.

A Fas ligand therapeutic agent including a variant, derivative, mutant, chimera, or analogue of a Fas ligand polypeptide, or a biologically active Fas ligand derived peptide therapeutic agent, can be made using the following exemplary expression systems. Below are some exemplary expression systems in bacteria, yeast, insects, and mammals. In the particular case of any of the Fas ligand polypeptides of the invention, the polypeptides can be expressed recombinantly by methods standard in the art, including using expression systems described herein, for example.

Expression Systems

Although the methodology described below is believed to contain sufficient details to enable one skilled in the art to practice the present invention, other constructs can be constructed and purified using standard recombinant DNA techniques as described in, for example, Sambrook et al. (1989), MOLECULAR CLONING: A LABORATORY MANUAL, 2nd ed. (Cold Spring Harbor Press, Cold Spring Harbor, N.Y.); and under current regulations described in United States Dept. of HHS, NATIONAL INSTITUTE OF HEALTH (NLH) GUIDELINES FOR RECOMBINANT DNA RESEARCH. The polypeptides of the invention can be expressed in any expression system, including, for example, bacterial, yeast, insect, amphibian and mammalian systems. Expression systems in bacteria include those described in Chang et al., $Nature$ (1978) 275: 615, Goeddel et al., $Nature$ (1979) 281: 544, Goeddel et al., $Nucleic Acids Res.$ (1980) 8: 4057, EP 36,776, U.S. Pat. No. 4,551,433, deBoer et al., $Proc. Natl. Acad. Sci. USA$ (1983) 80: 21–25, and Siebenlist et al., $Cell$ (1980) 20: 269. Expression systems in yeast include those described in Hinnen et al., $Proc. Natl. Acad. Sci. USA$ (1978) 75: 1929; Ito et al., $J. Bacteriol.$ (1983) 153: 163; Kurtz et al., $Mol. Cell. Biol.$ (1986) 6: 142; Kunze et al., $J. Basic Microbiol.$ (1985) 25: 141; Gleeson et al., $J. Gen. Microbiol.$ (1986) 132: 3459, Roggenkamp et al., $Mol. Gen. Genet.$ (1986) 202 :302) Das et al., $J. Bacteriol.$ (1984) 158: 1165; De Louvencourt et al., $J. Bacteriol.$ (1983) 154: 737, Van den Berg et al., $Bio/Technology$ (1990) 8: 135; Kunze et al., $J. Basic Microbiol.$ (1985) 25: 141; Cregg et al., $Mol. Cell. Biol.$ (1985) 5: 3376, U.S. Pat. No. 4,837,148, U.S. Pat. No. 4,929,555; Beach and Nurse, $Nature$ (1981) 300: 706; Davidow et al., $Curr. Genet.$ (1985) 10: 380, Gaillardin et al., $Curr. Genet.$ (1985) 10: 49, Ballance et al., $Biochem. Biophys. Res. Commun.$ (1983) 112: 284–289; Tilburn et al., $Gene$ (1983) 26: 205–221, Yelton et al., $Proc. Natl. Acad. Sci. USA$ (1984) 81: 1470–1474, Kelly and Hynes, $EMBO J.$ (1985) 4: 475479; EP 244,234, and WO 91/00357. Expression of heterologous genes in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., $J. Gen. Virol.$ (1988) 69: 765–776, Miller et al., $Ann. Rev. Microbiol.$ (1988) 42: 177, Carbonell et al., $Gene$ (1988) 73: 409, Maeda et al., $Nature$ (1985) 315: 592–594, Lebacq-Verheyden et al., $Mol. Cell. Biol.$ (1988) 8: 3129; Smith et al., $Proc. Natl. Acad. Sci. USA$ (1985) 82: 8404, Miyajima et al., $Gene$ (1987) 58: 273; and Martin et al., $DNA$ (1988) 7:99. Numerous baculoviral strains and variants and corresponding permissive insect host cells from hosts are described in Luckow et al., $Bio/Technology$ (1988) 6: 47–55, Miller et al., in GENERIC ENGINEERING (Setlow, J. K. et al. eds.), Vol. 8 (Plenum Publishing, 1986), pp. 277–279, and Maeda et al., $Nature$, (1985) 315: 592–594. Mammalian expression can be accomplished as described in Dijkema et al., $EMBO J.$ (1985) 4: 761, Gorman et al., $Proc. Natl. Acad. Sci. USA$ (1982b) 79: 6777, Boshart et al., $Cell$ (1985) 41: 521 and U.S. Pat. No. 4,399,216. Other features of mammalian expression can be facilitated as described in Ham and Wallace, $Meth. Enz.$ (1979) 58: 44, Barnes and Sato, $Anal.$ Biochem. (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Small Molecule Library Synthesis

The Fas ligand derived therapeutic agents can include small molecule mimics or agonists of Fas ligand activity. They can be screened for the ability to bind Fas, or bind and activate Fas expressed on a cell. Activation can be noted by the death of the cell contacted by the small molecule Fas ligand agonist. Small molecule agonists of Fas ligand activity, for example, a peptide, peptoid, or organic small molecule can be screened from a library for ability to bind Fas antigen, or additionally for the ability to bind and activate Fas antigen expressed on a cell for the purpose of inducing apoptosis in the Fas expressing cell.

Therapeutic agents of the invention can include peptides and peptoids derived from Fas ligand polypeptide sequence, and can be designed or modified to accomplish improved biological activity over Fas ligand polypeptide, such as, for example higher affinity for Fas ligand receptor, or resistance to degradation in the mammal. Peptides and peptoids can be prepared synthetically in libraries for screening for a favored biological activity, for example, increased binding to Fas ligand receptor. Exemplary synthesis of some of these small molecules are described below. The small molecules libraries designed based on variations in Fas ligand receptor binding sites of a Fas ligand polypeptide can be screened for ability to bind to Fas ligand receptor and induce apoptosis, for example, in a cell-base assay in microwell plates.

Small molecule libraries that are peptide and peptoid derivatives of Fas ligand are made as follows. A "library" of peptides may be synthesized and used following the methods disclosed in U.S. Pat. No. 5,010,175, (the '175 patent) and in PCT WO91/17823. In method of the '175 patent, a suitable peptide synthesis support, for example, a resin, is coupled to a mixture of appropriately protected, activated amino acids. The method described in WO91/17823 is similar but simplifies the process of determining which peptides are responsible for any observed alteration of gene expression in a responsive cell. The methods described in WO91/17823 and U.S. Pat. No. 5,194,392 enable the preparation of such pools and subpools by automated techniques in parallel, such that all synthesis and resynthesis may be performed in a matter of days.

Further alternative agents include small molecules, including peptide analogs and derivatives, that can act as stimulators or inhibitors of gene expression, or as ligands or antagonists. Some general means contemplated for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ. New York (1983). Moreover, substitution of D-amino acids for the normal L-stereoisomer can be carried out to increase the half-life of the molecule.

Peptoids, polymers comprised of monomer units of at least some substituted amino acids, can act as small molecule stimulators or inhibitors herein and can be synthesized as described in PCT 91/19735. Presently preferred amino acid substitutes are N-alkylated derivatives of glycine, which are easily synthesized and incorporated into polypeptide chains. However, any monomer units which allow for the sequence specific synthesis of pools of diverse molecules are appropriate for use in producing peptoid molecules. The benefits of these molecules for the purpose of the invention is that they occupy different conformational space than a peptide and as such are more resistant to the action of proteases.

Peptoids are easily synthesized by standard chemical methods. The preferred method of synthesis is the "submonomer" technique described by R. Zuckermann et al., J. Am. Chem. Soc. (1992) 114:10646–7. Synthesis by solid phase techniques of heterocyclic organic compounds in which N-substituted glycine monomer units forms a backbone is described in copending application entitled "Synthesis of N-Substituted Oligomers" filed on Jun. 7, 1995 and is herein incorporated by reference in full. Combinatorial libraries of mixtures of such heterocyclic organic compounds can then be assayed for the ability to alter gene expression.

Synthesis by solid phase of other heterocyclic organic compounds in combinatorial libraries is also described in copending application U.S. Ser. No. 08/485,006 entitled "Combinatorial Libraries of Substrate-Bound Cyclic Organic Compounds" filed on Jun. 7, 1995, herein incorporated by reference in full. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization as described in the same application.

Assays for Activity of Fas Ligand Therapeutic Agents

The Fas ligand therapeutic agents of the invention can be tested for binding of Fas in an in vitro assay or in vivo assay by contacting Fas with the Fas ligand therapeutic agent. The Fas ligand therapeutic agents can be tested for activation of Fas in a in vivo cell-based assay. In a cell-based assay, cells expressing Fas are cultured in the presence of the candidate Fas ligand therapeutic, and apoptosis of the cells represents a functional Fas ligand therapeutic agent. Such an assay for cytotoxic activity can be performed as described, for example, in Tanaka et al, *Nature Medicine* 2(3): 317–322 (1996). Alternatively, transcription of a gene known to be upregulated by activation of the Fas pathway can be measured, as an indicator of activation of Fas by binding to a ligand.

Where the Fas ligand therapeutic agent is a polynucleotide encoding a Fas ligand polypeptide, the polynucleotide can be expressed in the cells expressing Fas. Activation of Fas can be detected as just described. Alternatively, the polynucleotide can be expressed in a different population of cells, and either co-cultured with the Fas expressing cells, or the supernatants of the Fas ligand polypeptide expressing cells can be added to the Fas expressing cells.

Standard binding assays can be used to detect molecules capable of binding Fas, preferably the extracellular portion of Fas. Such binding can be detected by standard techniques, including labeled antibodies, or labeled Fas polypeptides, or labeled candidate molecules. Standard in vivo cell assays for detecting molecules capable of binding and activating Fas can be constructed using Fas expressing cell lines, and identifying apoptosis in cells that have contacted a molecule positive for the ability to bind and activate Fas. It is possible that the screening assays can be conducted by first screening for molecules that bind Fas, and from those molecules screening for molecules that also then activate Fas expressed on a cell.

Assays for determining whether a Fas ligand polypeptide has been constructed that is capable of remaining on the cell membrane longer than native Fas ligand can be conducted as described in Tanaka et al, *Nature Medicine* 2(3): 317–322 (1996) using anti-Fas ligand antibodies and making a comparison of staining intensity of mutant Fas ligand polypeptide with, for example, native Fas ligand expressed in the same cell type.

Diagnostic and Therametric Procedures

Practice of the invention may begin by diagnosing the mammal as is appropriate for the particular autoimmunity they may be exhibiting. The diagnosis may also continue during treatment, as a therametric procedure, to monitor the progress of treatment, and to direct modification of such parameters as the dosage or frequency in continued treatments, for example. Additional diagnosis that might aid in determining appropriateness for administration of a Fas ligand therapeutic agent include an analysis of expression levels of Fas in the mammals lymphocytes, and a comparison of these levels between lymphocytes distal from the site of autoimmunity, and those proximal to the site or autoimmunity. The autoimmune disease in the mammal being treated can be monitored by detecting Fas antigen on a cell surface. This monitoring can include contacting a sample of the mammal's lymphocytes with a Fas-specific antibody, and detecting binding of the antibody to the sample.

Gene Delivery Vehicles

Gene therapy vehicles for delivery of constructs including a coding sequence of a therapeutic of the invention, to be delivered to the mammal for expression in the mammal, for example, a Fas ligand coding sequence, or also including a nucleic acid sequence of all or a portion of Fas ligand for delivery can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. Where the Fas ligand is expressed in the mammal, it can be expressed as soluble Fas ligand, or as a membrane-bound Fas ligand, both or either including, for example, all of the Fas ligand, or a biologically active portion, variant, derivative or fusion of Fas ligand.

The invention includes gene delivery vehicles capable of expressing the contemplated Fas ligand nucleic acid sequences. The gene delivery vehicle is preferably a viral vector and, more preferably, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. See generally, Jolly, *Cancer Gene Therapy* 1 (1994) 51–64, Kimura, *Human Gene Therapy* 5 (1994) 845–852, Connelly, *Human Gene Therapy* 6 (1995) 185–193 and Kaplitt, *Nature Genetics* 6 (1994) 148–153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill, *J. Vir.* 53 (1985) 160) polytropic retroviruses (for example, MCF and MCF-MLV (see Kelly, *J. Vir.* 45 (1983)291), spumaviruses and lentiviruses. See *RNA Tumor Viruses*, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Ser. No. 07/800,921, filed Nov. 29, 1991). Retrovirus vectors can be constructed for site-specific integration into host cell DNA by incorporation of a chimeric integrase enzyme into the retroviral particle. See, U.S. Ser. No. 08/445,466 filed May 22, 1995. It is preferable that the recombinant viral vector is a replication defective recombinant virus.

Packaging cell lines suitable for use with the above-described retrovirus vectors are well known in the art, are readily prepared (see U.S. Ser. No. 08/240,030, filed May 9, 1994; see also WO 92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe, *J. Virol* 19 (1976) 19–25), Abelson (ATCC No. VR-999), Friend (ATCC No. VR-245), Graffi, Gross (ATCC No. VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Maryland or isolated from known sources using commonly available techniques.

Exemplary known retroviral gene therapy vectors employable in this invention include those described in GB 2200651, EP 0415731, EP 0345242, WO 89/02468; WO 89/05349, WO 89/09271, WO 90/02806, WO 90/07936, WO 90/07936, WO 94/03622, WO 93/25698, WO 93/25234, WO 93/11230, WO 93/10218, WO 91/02805, in U.S. Pat. No. 5,219,740, U.S. Pat. No. 4,405,712, U.S. Pat. No. 4,861,719, U.S. Pat. No. 4,980,289 and U.S. Pat. No. 4,777,127, in U.S. Ser. No. 07/800,921 and in Vile, *Cancer Res* 53 (1993) 3860–3864, Vile, *Cancer Res* 53 (1993) 962–967, Ram, *Cancer Res* 53 (1993) 83–88, Takamiya, *J Neurosci Res* 33 (1992) 493–503, Baba, *J Neurosurg* 79 (1993) 729–735, Mann, *Cell* 33 (1983)153, Cane, *Proc Natl Acad Sci* 81 (1984) 6349 and Miller, *Human Gene Therapy* 1 (1990).

Human adenoviral gene therapy vectors are also known in the art and employable in this invention. See, for example, Berkner, *Biotechniques* 6 (1988) 616, and Rosenfeld, *Science* 252 (1991) 431, and WO 93/07283, WO 93/06223, and WO 93/07282. Exemplary known adenoviral gene therapy vectors employable in this invention include those described in the above referenced documents and in WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922 and WO 95/09654. Alternatively, administration of DNA linked to killed adenovirus as described in Curiel, *Hum. Gene Ther.* 3 (1992)147–154 may be employed.

The gene delivery vehicles of the invention also include adenovirus associated virus (AAV) vectors. Leading and preferred examples of such vectors for use in this invention are the AAV-2 basal vectors disclosed in Srivastava, WO 93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini, *Gene* 124 (1993) 257–262. Another example of such an AAV vector is psub201. See Samulski, *J. Virol.* 61 (1987) 3096. Another exemplary AAV vector is the Double-D ITR vector. How to make the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication WO 94/288157. Yet a further example of an AAV vector employable in this invention is SSV9AFABTKneo, which contains the AFP enhancer and albumin promoter and directs expression predominantly in the liver. Its structure and how to make it are disclosed in Su, *Human Gene Therapy* 7(1996) 463–470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP 0176170 (Roizman). Additional exemplary herpes simplex virus vectors include HFEM/ICP6-LacZ disclosed in WO 95/04139 (Wistar Institute), pHSVlac described in Geller, *Science* 241 (1988)1667–1669 and in WO 90/09441 and WO 92/07945, HSV Us3::pgClacZ described in Fink, *Human Gene Therapy* 3 (1992) 11–19 and HSV 7134, 2 RH 105 and GAL4 described in EP 0453242 (Breakefield), and those deposited with the ATCC as accession numbers ATCC VR-977 and ATCC VR-260.

We also contemplate that alpha virus gene therapy vectors may be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO 92/10578. More particularly, those alpha virus vectors described in U.S. Ser. No. 08/405,627, filed Mar. 15, 1995 and U.S. Ser. No. 08/198,450 and in PCT Patent Publications WO 94/21792, WO 92/10578, WO 95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see co-owned U.S. Ser. No. 08/679640).

DNA vector systems such as eukarytic layered expression systems are also useful for expressing the Fas ligand nucleic acids of the invention. See WO 95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339 (1989) 385 and Sabin, *J. Biol. Standardization* 1 (1973) 115; rhinovirus, for example ATCC VR-1110 and those described in Arnold, *J Cell Biochem* (1990) L401; pox viruses such as canary pox virus or vaccinia virus, for example ATCC VR-111 and ATCC VR-2010 and those described in Fisher-Hoch, *Proc Natl Acad Sci* 86 (1989) 317, Flexner, *Ann NY Acad Sci* 569 (1989) 86, Flexner, *Vaccine* 8 (1990) 17; in U.S. Pat. No. 4,603,112 and U.S. Pat. No. 4,769,330 and in WO 89/01973; SV40 virus, for example ATCC VR-305 and those described in Mulligan, *Nature* 277 (1979) 108 and Madzak, *J Gen Vir* 73 (1992) 1533; influenza virus, for example ATCC VR-797 and recombinant influenza viruses made employing reverse genetics techniques as described in U.S. Pat. No. 5,166,057 and in Enami, Proc Natl Acad Sci 87 (1990) 3802–3805, Enami and Palese, J Virol 65 (1991) 2711–2713 and Luytjes, Cell 59 (1989) 110, (see also McMicheal., NE J Med 309 (1983) 13, and Yap, *Nature* 273 (1978) 238 and *Nature* 277 (1979) 108); human immunodeficiency virus as described in EP 0386882 and in Buchschacher, *J. Vir.* 66 (1992) 2731; measles virus, for example ATCC VR-67 and VR-1247 and those described in EP 0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre, *Proc Soc Exp Biol Med* 121 (1966)190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel, *Hum Gene Ther* 3 (1992) 147–154 ligand linked DNA, for example see Wu, *J Biol Chem* 264 (1989) 16985–16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO 92/11033, nucleic charge neutralization or fusion with cell membranes. Additional approaches are described in Philip, *Mol Cell Biol* 14 (1994) 2411–2418 and in Woffendin, *Proc Natl Acad Sci* 91 (1994) 1581–585.

Particle mediated gene transfer may be employed, for example see U.S. Ser. No. 60/023,867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, *J. Biol. Chem.* 262 (1987) 4429–4432, insulin as described in Hucked, *Biochem Phannacol* 40 (1990) 253–263, galactose as described in Plank, *Bioconjugate Chem* 3 (1992) 533–539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO 95/13796, WO 94/23697, WO 91/144445 and EP 524,968. As described in co-owned U.S. Ser. No. 60/023,867, on non-viral delivery, the nucleic acid sequences encoding a Fas ligand polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., *Proc. Natl. Acad. Sci. USA* (1994) 91(24): 11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO 92/11033

Exemplary liposome and polycationic gene delivery vehicles are those described in U.S. Pat. Nos. 5,422,120 and 4,762,915, in WO 95/13796, WO 94/23697, and WO 91/14445, in EP 0524968 and in Stryer, *Biochemistry*, pages 236–240 (1975) W.H. Freeman, San Francisco, Szoka, *Biochem Biophys Acta* 600 (1980) 1, Bayer, *Biochem Biophys Acta* 550 (1979) 464, Rivnay, Meth Enzymol 149 (1987) 119, Wang, *Proc Natl Acad Sci* 84 (1987) 7851, Plant, *Anal Biochem* 176 (1989) 420.

Pharmaceutical Compositions and Therapeutic Methods

The invention discloses a method of treating mammals afflicted with an autoimmune disease that includes activated lymphocytes, including activated T-cells or activated B-cells, by administration of a Fas ligand or Fas ligand derived therapeutic agent, for example, either Fas ligand polypeptide as a therapeutic agent or a polynucleotide encoding a Fas ligand polypeptide for expression in the mammal, or a small molecule Fas ligand agonist therapeutic agent Autoimmune diseases that can be treated by the method and compositions of the invention include any autoimmune disease, or transplantation rejection, including, but not limited to, for example, those autoimmune diseases listed herein.

Fas ligand can be administered, for example, as a recombinantly expressed polypeptide, or as a variant, derivative, or fusion protein of Fas ligand polypeptide, delivered either locally or systemically to the mammal. DNA or RNA encoding Fas ligand, or a derivative or variant of Fas ligand, or a Fas ligand fusion, can be administered in a gene therapy protocol, as naked plasmid DNA including regulatory regions for expression in the mammal, or in a viral vector for expression in the mammal. Delivery of Fas ligand polypeptide for expression can be accomplished with a pharmaceutically acceptable carrier capable of facilitating the delivery. Treatment of a mammal having an autoimmune disease with a Fas ligand derived therapeutic agent can result in amelioration or remission or the autoimmune disease, or in absence of clinical symptoms attributable to the autoimmunity.

Although the invention is not limited to theories of how the invention works, it is posited by the inventor that activated T-cells and B-cells that cause the self-recognition and subsequent harm in autoimmunity express Fas. By expressing Fas ligand or causing Fas ligand to be expressed, or by administering a Fas ligand derived therapeutic agent, the activated lymphocytes expressing Fas are preferentially targeted for apoptosis by binding the Fas ligand moiety made available. The Fas ligand polypeptide or a Fas ligand derived therapeutic agent can be administered in the region exhibiting the autoimmunity, for example, in the localized region that characterized the particular autoirnmune disease being treated. This optimizes the contact between the administered Fas ligand or other therapeutic agent and the Fas expressing activated T-cells and B-cells which are specific for the self antigens expressed on the cells of that region. The cells of the region are thus also good candidates for expressing, by aid of a gene delivery vehicle, a polynucleotide encoding a Fas ligand polypeptide administered to the region. Thus, in various permutations and applications of the invention, the expression of the Fas ligand polypeptide can be recombinantly engineered to facilitate expression in cells that are under attack by the activated T-cells and B-cells. In the case of transplantation rejection, the inventor proposes a Fas ligand polypeptide fusion with a binding portion of a molecule capable of binding a protein ubiquitously expressed on the cell surfaces of many cell types. This binding portion can be, for example, heparin, and the molecule on the cell surface to which it binds can be a glycosaminoglycan. Alternatively, the binding portion may be a single chain antibody binding domain, specific for any selected cell surface antigen. The expressed and purified fusion protein of a Fas binding portion of Fas ligand and glycosaminoglycan binding portion of heparin can be administered to an organ, tissue or cell in preparation for a transplant, and upon transplantation, the organ, tissue or cell has Fas ligand polypeptide portions available as a first line of defense against activated T-cells or B-cells which would otherwise attack and immunologically reject the allograft.

"Administration" or "administering" as used herein refers to the process of delivering to a mammal a therapeutic agent, or a combination of therapeutic agents. The process of administration can be varied, depending on the therapeutic agent, or agents, and the desired effect. Administration can be accomplished by any means appropriate for the therapeutic agent, for example, by parenteral or oral delivery. The parenteral delivery can be, for example, subcutaneous, intravenous, intramuscular, intra-arterial, injection into the tissue of an organ, mucosal, pulmonary, topical, or catheter-based. Oral means is by mouth, including pills or other gastroenteric delivery means, including a drinkable liquid. Mucosal delivery can include, for example, intranasal delivery. Pulmonary delivery can include inhalation of the agent. Catheter-based delivery can include delivery by iontophoretic catheter-based delivery. Administration generally also includes delivery with a pharmaceutically acceptable carrier., such as, for example, a buffer, a polypeptide, a peptide, a polysaccharide conjugate, a liposome, and a lipid. A gene therapy protocol is considered an administration in which the therapeutic agent is a polynucleotide capable of accomplishing a therapeutic goal when expressed as a transcript or a polypeptide in the mammal, and can be applied to both parenteral and oral delivery means. Such administration means are selected as appropriate for the disease being treated. For example, where the disease is organ-based, delivery may be local, and for example, where the disease is systemic, the delivery may be systemic.

"Co-administration" refers to administration of one or more therapeutic agents in course of a given treatment of a patient. The agents may be administered with the same pharmaceutical carrier, or different carriers. They may be administered by the same or different administration means. The agents may be the same type of agent or different types of agents, for example, different types can include polynucleotides, polypeptide, or small molecules. The time of administration may be exactly the same time, or one therapeutic agent may be administered before or after another agent. Thus a co-administration can be simultaneous, or consecutive. The exact protocol for a given combination of therapeutic agents is determined considering the agents and the condition being treated, among other considerations.

The term "in vivo administration" refers to administration to a patient, for example a mammal, of a polynucleotide encoding a polypeptide for expression in the mammal. In particular, direct in vivo administration involves transfecting a mammal's cell with a coding sequence without removing the cell from the mammal. Thus, direct in vivo administration may include direct injection of the DNA encoding the polypeptide of interest in the region afflicted by the autoimmune disease, resulting in expression in the patient's cells.

The term "ex vivo administration" refers to transfecting a cell, for example, a cell from a population of cells that are under autoimmune attack, after the cell is removed from the patient, for example a mammal. After transfection the cell is then replaced in the mammal. Ex vivo administration can be accomplished by removing cells from a mammal, optionally selecting for cells to transform, (i.e. cells under attack by an autoimmune mechanism) rendering the selected cells incapable of replication, transforming the selected cells with a polynucleotide encoding a gene for expression, (i.e. Fas ligand), including also a regulatory region for facilitating the expression, and placing the transformed cells back into the patient for expression of the Fas ligand.

A "therapeutically effective amount" is that amount that generates the desired therapeutic outcome. For example, if the therapeutic effect desired is a remission from autoimmunity, the therapeutically effective amount is that amount that facilitates the remission. A therapeutically effective amount can be an amount administered in a dosage protocol that includes days or weeks of administration, for example. Where the therapeutic effect is a reduction of the effects of an autoimmune response in the mammal, for example, during the manifestations of symptoms of an autoimmune disease, the effective amount of an agent to accomplish this in the mammal is that amount that results in reduction of the symptoms of autoimmunity.

The term "pharmaceutically acceptable carrier" refers to a carrier for administration of a therapeutic agent, such as, for example, a polypeptide, polynucleotide, small molecule, peptoid, or peptide, refers to any pharmaceutically acceptable carrier that does not itself induce the production of antibodies harmful to the individual receiving the composition, and which may be administered without undue toxicity. Within another aspect of the invention, pharmaceutical compositions are provided, comprising a recombinant viral vector as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for either surface administration, injection, oral, or rectal administration. Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 mg of material, it may be less than 1% of high molecular weight material, and less than 1/100,000 of the total material (including water). This composition is stable at −70° C. for at least six months.

Pharmaceutical compositions of the present invention may also additionally include factors which stimulate cell division, and hence, uptake and incorporation of a recombinant retroviral vector. Preserving recombinant viruses is described in U.S. applications entitled "Methods for Preserving Recombinant Viruses" (U.S. Ser. No. 08/135,938, filed Oct. 12, 1993) which is incorporated herein by reference in full.

All of the therapeutic agents that make up the proposed therapy of the invention can be incorporated into an appropriate pharmaceutical composition that includes a pharmaceutically acceptable carrier for the agent. The pharmaceutical carrier for the agents may be the same or different for each agent. Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Pharmaceutical compositions are provided comprising a recombinant retrovirus or virus carrying one of the above-described vector constructs, in combination with a pharmaceutically acceptable carrier or diluent. The composition may be prepared either as a liquid solution, or as a solid form (e.g., lyophilized) which is suspended in a solution prior to administration. In addition, the composition may be prepared with suitable carriers or diluents for either surface administration, injection, oral, or rectal administration.

Pharmaceutically acceptable carriers or diluents are non-toxic to recipients at the dosages and concentrations employed. Representative examples of carriers or diluents for injectable solutions include water, isotonic saline solutions which are preferably buffered at a physiological Ph (such as phosphate-buffered saline or Tris-buffered saline), mannitol, dextrose, glycerol, and ethanol, as well as polypeptides or proteins such as human serum albumin. A vector or recombinant virus can be delivered in a pharmaceutical composition in 10 mg/ml mannitol, 1 mg/ml HSA, 20 Mm Tris, Ph 7.2, and 150 Mm NaCl. In this case, since the recombinant vector represents approximately 1 g of material, it may be less than 1% of high molecular weight material, and less than $1/100,000$ of the total material (including water). This composition is stable at $-70°$ C. for at least six months.

The pharmaceutically acceptable carrier or diluent may be combined with the gene delivery vehicles to provide a composition either as a liquid solution, or as a solid form (e.g., lyophilized) which can be resuspended in a solution prior to administration. The two or more gene delivery vehicles are typically administered via traditional direct routes, such as buccal/sublingual, rectal, oral, nasal, topical, (such as transdermal and ophthalmic), vaginal, pulmonary, intraarterial, intramuscular, intraperitoneal, subcutaneous, intraocular, intranasal or intravenous, or indirectly.

Any therapeutic of the invention, including, for example, polynucleotides for expression in the mammal, can be formulated into an enteric coated tablet or gel capsule according to known methods in the art. These are described in the following patents: U.S. Pat. No. 4,853,230, EP 225, 189, AU 9,224,296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by antibodies to the expressed or non-expressed proteins.

The gene delivery vehicle can be introduced into a mammal, for example, by injection, particle gun, topical administration, parental administration, inhalation, or iontophoretic delivery, as described in U.S. Pat. No. 4,411,648 and U.S. Pat. No. 5,222,936, U.S. Pat. No. 5,286,254; and WO 94/05369.

A therapeutic composition or therapeutic agent can be administered with other therapeutic agents capable of ameliorating the autoimmune disease, or capable of enhancing the therapeutic benefits of administration of a Fas ligand therapeutic agent. For example, administration for treatment of an allergic reaction can be by aerosol administration of Fas ligand polynucleotide for expression in the cells present in mucosal, nasal, bronchial or lung tissue, and may be most favorably administered in repeat administrations, for example by nasal or aerosol spray several times daily for a period of time until the allergic reaction subsides.

The gene delivery vehicle may be administered at single or multiple sites to a mammal directly, for example by direct injection, or alternatively, through the use of target cells transduced ex vivo. The present invention also provides pharmaceutical compositions (including, for example, various excipients) suitable for administering the gene delivery vehicles.

A vector construct which directs the expression of a Fas ligand polypeptide, variant, derivative, analogue, mutant, or chimera can be directly administered to a site exhibiting autoimmunity, for example the pancreas, kidney, liver, joints, brain, the spinal fluid, skin, or other region or organ of the body. Various methods may be used within the context of the present invention in order to directly administer the vector construct. For example, arteries which serve the region may be identified, and the vector injected into such an artery, in order to deliver the vector directly into the site. Similarly, the vector construct may be directly administered to the skin surface, for example, by application of a topical pharmaceutical composition containing the vector construct.

In a direct administration, combination therapeutic agents including a Fas ligand therapeutic agent and other anti-autoimmune agents can be administered together. The co-administration can be simultaneous, achieved for example by placing polynucleotides encoding the agents in the same vector, or by putting the agents, whether polynucleotide, polypeptide, or other drug, in the same pharmaceutical composition, or by administering the agents in different pharmaceutical compositions injected at about the same time, and perhaps in the same location. If the co-administration is not simultaneous, for example, in the case of administration of the prodrug after administration of the prodrug activator, the second agent can be administered by direct injection as appropriate for the goals of the therapy. Thus, for example, in the case of an administration of a prodrug, the prodrug is administered at the same location as the prodrug activator. Thus, a co-administration protocol can include a combination of administrations to achieve the goal of the therapy. Further, the co-administration can include subsequent administrations as is necessary, for example, repeat in vivo direct injection administrations of a Fas ligand.

Within the context of the present invention, it should be understood that the removed cells may be returned to the same animal, or to another allogenic animal or mammal. In such a case it is generally preferable to have histocompatibility matched animals (although not always, see, e.g., Yamamoto et al., "Efficacy of Experimental FIV Vaccines," 1st International Conference of FIV Researchers, University of California at Davis, September 1991.

Cells may be removed from a variety of locations in the patient. In addition, within other embodiments of the invention, a vector construct may be inserted into, for example, cells from the skin (dermal fibroblasts), or from the blood (e.g., peripheral blood leukocytes). If desired particular fractions of cells such as a T cell subset or stem cells may also be specifically removed from the blood (see, for example, PCT WO 91/16116, an application entitled "Immunoselection Device and Method"). Vector constructs may then be contacted with the removed cells utilizing any of the above-described techniques, followed by the return of the cells to the warm-blooded animal, preferably to or within the vicinity of the region exhibiting autoinmunity.

Once the patient, for example a mammal, has been diagnosed, practice of the invention includes providing a Fas ligand therapeutic agent, and administering it to the mammal in a manner and dose appropriate for the particular autoimmune disease being treated, and monitoring the mammal for determining the need for continued or modified administrations of the therapeutic agent. Practice of the invention is accomplished by identifying the disease to be treated, and determining the probable cell-type or region of the body to which a targeted gene therapy can be applied. The Fas ligand polynucleotide is constructed, including either a plasmid with regulatory regions for expression in the mammal, or a viral vector for the expression. Some of the mammal's cells can be removed, transfected with the polynucleotide encoding Fas ligand, and replaced into the mammal for expression of Fas ligand. Alternatively the polynucleotide can be administered to the mammal, for example in the region where the disease is manifest, for expression in the mammal's cells in that region.

Thus, for example, in the case of rheumatoid arthritis, the sinovoid cells can be transfected ex vivo with Fas ligand, or Fas ligand in a gene delivery vehicle can be administered to the joints which includes large populations of sinovoid cells, for expression of the Fas ligand polypeptide in these cells.

For example, in treatment of multiple sclerosis, Fas ligand can be injected into the region of the brain being effected, or in the spinal fluid, to facilitate expression of Fas ligand in the cells that are under attack by the activated T-cells or B-cells in an autoimmune type of reaction. Also, by example, in the case of multiple sclerosis, Fas ligand DNA can be locally injected into the mammal's brain, or oligodendrites from the spinal fluid can be removed, transfected with Fas ligand DNA, and returned to the region of the spinal cord.

Further by example, for treating a mammal having Sojgren's syndrome, the organ targeted by the disease is selected for administration Fas ligand polypeptide by injection. Also, by example, for mammal's suffering from Sojgren's syndrome, the affected organ can be identified, for example the kidney, and Fas ligand DNA administered to the organ directly, or cells from the organ removed, transfected, and replaced in the body for expression of Fas ligand in those cells in the mammal.

For example, in the case of preventing transplantation rejection, the animal to receive the transplant can receive localized or systemic administration of a Fas ligand therapeutic agent in order to kill any activated patient cells that express Fas which attacks the foreign cells, tissue or organ, or a Fas ligand polypeptide can be expressed in cells on the external surface of the organ just prior to the transplant, in order the protect the organ once inside the patient's body. Continued administration of the Fas ligand therapeutic agent may be necessary while the recipient's immune system adjusts to the foreign cells, tissue or organ.

The Fas ligand therapeutic agent is expected to act analogously to native Fas ligand. Accordingly, it will trimerize Fas to cause an apoptotic reaction in the cells expressing Fas. Thus, stoichiometrically, the clinician would be able to be aware of the amount of Fas ligand that needs to be expressed or otherwise administered to the mammal for achieving the desired activation of Fas and subsequent death of the cell that expressed Fas. Various proposed mechanisms of action of Fas ligand are explained and the production of Fas ligand is described in EP 675 200, incorporated by reference in full. Within other aspects of the present invention, the vector constructs described herein may also direct the expression of additional non-vector derived genes.

For example, a prodrug system applied in conjunction with administration of Fas ligand can act as a safety mechanism for the gene therapy, or can act as a combination therapeutic agent. As a safety mechanism, the prodrug activator, for example HSV TK, is expressed in a vector along with the Fas ligand. When it is determined that the system should be arrested, the prodrug, for example gancyclovir, is administered and HSV TK activates gancyclovir, which kills the cells expressing Fas. This allows the clinician a measure of control over the gene therapy. The HSV TK/gancyclovir system may be useful for inactivating the transfected cells in the mammal, where, for example, the autoimmunity is exacerbated by the Fas ligand expression. The HSV TK/gancyclovir system can also be administered as combination therapeutic agent, in a combination therapy protocol, for achieving cell killing using the prodrug activation provided by the HSV TK/gancyclovir system as just described.

The therapy including administration of a polynucleotide encoding a Fas ligand polypeptide, in conjunction with a prodrug activator and prodrug, can also be immunomodulatory. "Inununomodulatory" refers to use of factors which, when manufactured by one or more of the cells involved in an immune response, or, which when added exogenously to the cells, causes the immune response to be different in quality or potency from that which would have occurred in the absence of the factor. The quality or potency of a response may be measured by a variety of assays known to one of skill in the art including, for example, in vitro assays which measure cellular proliferation (e.g., $^{3}$H thymidine uptake), and in vitro cytotoxic assays (e.g., which measure $^{51}$Cr release) (see, Warner et al., *AIDS Res. and Human Retroviruses* 7:645–655, 1991). Immunomodulatory factors may be active both in vivo and ex vivo. Representative examples of such factors include cytokines, such as interleukins 2, 4, 6, 12 and 15 (among others), alpha interferons, beta interferons, gamma interferons, GM-CSF, G-CSF, and tumor necrosis factors (TNFs). Other immunomodulatory factors include, for example, CD3, ICAM-1, ICAM-2, LFA-1, LFA-3, MHC class I molecules, MHC class II molecules, B7.1-.3, $b_2$-microglobulin, chaperones, or analogs thereof. If the gene delivery vehicle, however, does not express an immunomodulatory cofactor which is a cytokine, this cytokine may be included in the above-described compositions, or may be administered separately (concurrently or subsequently) with the above-described compositions. Briefly, within such an embodiment, the immunomodulatory cofactor is preferably administered according to standard protocols and dosages as prescribed in *The Physician's Desk Reference*. For example, alpha interferon may be administered at a dosage of 1–5 million units/day for 2–4 months, and IL-2 at a dosage of 10,000–100,000 units/kg of body weight, 1–3 times/day, for 2–12 weeks. Gamma interferon may be administered at dosages of 150,000–1,500,000 units 2–3 times/week for 2–12 weeks for example, for upregulating Fas expression in activated T-cells for achieving more effective therapy with the administration of Fas ligand.

As a combination therapeutic agent, the prodrug activator can be expressed from its own vector, or from the same vector as the Fas ligand polypeptide. Either vector system (a single vector, or two vectors) can be administered by in vivo or ex vivo means. In an autoimmune therapy, for example, the addition of HSV TK or other prodrug activator facilitates further immunomodulatory effect supporting the effect achieved by Fas ligand and in addition, addition of the prodrug can activate the killing of transfected cells.

A chaperon molecule can be administered before, contemporaneously with or after administration of the polynucleotide therapeutic, and the chaperon molecule can be, for example, a heat shock protein, such as, for example hsp70. Further, the polynucleotide being expressed in the mammal can be linked to an inducible promoter, for example a tissue specific promoter, for the purpose of, for example, ensuring expression of the polynucleotide only in the desired target cells. Additionally, for the purpose of effectively delivering the polynucleotide to a tissue, the polynucleotide can be flanked by nucleotide sequences suitable for integration into genome of the cells of that tissue.

For this and many other aspects of the invention, effectiveness of treating humans may first be tested in animal models for a given autoimmune disease. Such existing animal models include those for the following autoimmune disease: Sjogren's syndrome (autoimmune dacryodentis or immune-mediated sialadenitis), autoimmune myocarditis, primary biliary cirrhosis (PBC), inflammatory heart disease, mercury-induced renal autoimmunity, insulin dependent diabetes mellitus (type I diabetes or IDD), post-thymectomy autoimmunity, a central nervous system (CNS) demyelination disorder, CNS lupus, narcolepsy, myasthenia gravis (MG), Grave's disease, a immune-mediated PNS disorder, osteoarthritis, rheumatoid arthritis, uveitis, medullary cystic fibrosis, autoimmune hemolytic disease, autoimmune vasculitis, ovarian autoimmune disease, and human schleroderma.

The multiple gene delivery vehicles may be administered to animals or plants. In preferred embodiments, the animal is a warm-blooded animal, further preferably selected from the group consisting of mice, chickens, cattle, pigs, pets such as cats and dogs, horses, and humans.

For polypeptide therapeutics, for example, Fas ligand or other cytokine, the dosage can be in the range of about 5 μg to about 50 μg/kg of mammal body weight, also about 50 μg to about 5 mg/kg, also about 100 μg to about 500 μg/kg of mammal body weight, and about 200 to about 250 ug/kg.

For polynucleotide therapeutics, for example a polynucleotide encoding a native or mutant Fas ligand polypeptide, depending on the expression of the polynucleotide in the patient, for example a mammal, for tissue targeted administration, vectors containing expressible constructs of coding sequences, or non-coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

For administration of small molecule therapeutics, depending on the potency of the small molecule, the dosage may vary. For a very potent inhibitor, microgram (μ) amounts per kilogram of mammal may be sufficient, for example, in the range of about 1 μg/kg to about 500 mg/kg of mammal weight, and about 100 μg/kg to about 5 mg/kg, and about 1 μg/kg to about 50 μg/kg, and, for example, about 10 ug/kg. For administration of peptides and peptoids the potency also affects the dosage, and may be in the range of about 1 μg/kg to about 500 mg/kg of mammal weight, and about 100 μg/kg to about 5 mg/kg, and about 1 μg/kg to about 50 μg/kg, and a usual dose might be about 10 ug/kg.

In all cases, routine experimentation in clinical trials would narrow the therapeutic range for optimal therapeutic effect, for each therapeutic, each administrative protocol, and administration to specific mammals will also be adjusted to within effective and safe ranges depending on the mammal condition and responsiveness to initial administrations.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description. Also, the invention is not limited by any theories of mechanism of the method of the invention.

The present invention is illustrated by reference to the following examples which set forth particularly advantageous embodiments. However, it should be noted that these embodiments are illustrative and are not to be construed as restricting the invention in any way.

EXAMPLE 1

A human patient with rheumatoid arthritis is diagnosed. The sinovoid cells of the patient are targeted for therapy. A population of the sinovoid cells of the patient are removed and transfected with a polynucleotide (SEQ ID NO: 5 or 9) encoding a non-cleavable Fas ligand (e.g., SEQ ID NO: 6 or 10) under control of a temperature sensitive promoter. The transfected ex vivo cells are replaced into the region of the patient's joints from which they were removed. Heating pads are applied to the patient's joints to induce expression of non-cleavable membrane bound Fas ligand. The patient is monitored for reduction in symptoms.

EXAMPLE 2

A patient is diagnosed with multiple sclerosis. An adeno-associated viral (AAV) vector and its necessary components is prepared having a polynucleotide sequence encoding a Fas ligand polypeptide fusion protein capable of remaining on the cell membrane longer than native Fas ligand. This AAV is injected into the spinal fluid of the patient, and also into regions of the brain. Repeat administrations are directed as the patient is monitored for improvement.

EXAMPLE 3

A human patient is diagnosed as having Sojgren's syndrome manifested in the kidney. A Fas ligand polynucleotide is prepared in a plasmid under regulatory control of a kidney specific promoter. The plasmid DNA is encapsulated in liposomes, and the composition is administered directly to several regions of the kidney. The patient is monitored for improvement, and for readministration of the Fas ligand as directed by the progress.

EXAMPLE 4

A Fas ligand chimera is constructed by replacing the putative cleavage portion of Fas ligand with an uncleavable fragment from a similar region of a polypeptide of the same family. A 17 residue portion of Fas ligand between residues L127 to R144 is replaced with a 17 residue Fas ligand molecule corresponds to the wild type fragment of CD30 ligand from S83 to A100. The remainder of the Fas ligand molecule corresponds to the wild type Fas ligand sequence. The resulting fusion polypeptide remains membrane bound longer than native Fas.

EXAMPLE 5

Fas Ligand$_{30 \rightarrow 142}$ Deletion Mutein

A cDNA fragment (SEQ ID NO: 1) encoding the first 129 residues of Fas ligand (from M1 to Q130), designated as the "MQ" fragment was isolated and amplified using standard PCR techniques. A second cDNA fragment (SEQ ID NO: 3) encoding residues 143 to 281 of Fas ligand (from L143 to the stop codon), designated as the "LT" fragment, was isolated and amplified using standard PCR techniques.

The 3' end of the MQ fragment was ligated to the 5' end of the LT fragment MQ/LT using a standard ligase reaction to produce polynucleotide (SEQ ID NO: 5) encoding the Fas ligand 130→142 deletion mutein.

The MQ/LT polynucleotide is cloned into an appropriate high titer retroviral vector, such as pLNL6 [Bender, et al., (1987) *J. Virol.*, 61(5):1639–1646 or U.S. Pat. No. 5,324,655, which are hereby incorporated herein by reference] or a commercially available vector that is capable of infecting a mammalian host cell, preferably a human host cell. The transfected or transduced host cell is cultured whereupon the non-cleavable Fas ligand$_{130\rightarrow142}$ deletion mutein (i.e., a mutein lacking residues +1 to +12 from the P1 site) is expressed in said host cell and remains surface bound thereto.

EXAMPLE 6

Fas Ligand$_{130\rightarrow145}$ Deletion Mutein

The cDNA fragment (SEQ ID NO: 1) encoding the first 129 residues of Fas ligand (from M1 to Q130), designated as the "MQ" fragment was isolated and then amplified using standard PCR techniques. A second DNA fragment (SEQ ID NO: 7) encoding residues 146 to 281 of Fas ligand (from V146 to the stop codon), designated as the "VT" fragment.

The 3' end of the MQ fragment was ligated to the 5' end of the VT fragment using a standard ligase reaction to produce the MQ/VT polynucleotide (SEQ ID NO: 9) encoding the Fas ligand 130→145 deletion mutein.

The MQ/VT polynucleotide is cloned into an appropriate high titer retroviral vector, such as pLNL6 [Bender et al., (1987), *J. Virol.*, 61(5):1639–1646 or U.S. Pat. No. 5,324,655, both of which are hereby incorporated herein by reference] or a commercially available expression vector that is capable of infecting a mammalian host cell. The transfected or transduced host cell is cultured, whereupon the non-cleavable Fas ligand$_{130\rightarrow145}$ deletion mutein (i.e., a mutein lacking residues +1 to +15 from the P1 site) is expressed in the host cell and remains surface bound thereto.

What is claimed:

1. A Fas ligand agonist selected from the group consisting of a Fas ligand deletion mutein and a Fas ligand chimera, said Fas ligand deletion mutein being a deletion mutein of pro-Fas ligand lacking a continuous segment of 10 to 17 amino acid residues beginning at residue position 130 of pro-Fas ligand (SEQ ID NO: 12), said Fas ligand chimera being a fusion protein having an amino acid sequence that corresponds to the fusion product of the carboxy terminus of a transmembrane domain of a cell surface protein other than Fas ligand, said transmembrane domain being substantially non-cleavable from a cell membrane by proteinases or convertases and being fused to the amino terminus of the extracellular domain of Fas ligand, said extracellular domain lacking a continuous segment of 10 to 17 amino acid residues beginning at about residue position 130 of pro-Fas ligand (SEQ ID NO: 12).

2. The Fas ligand agonist of claim 1, wherein said Fas ligand deletion mutein is membrane bound.

3. The Fas ligand agonist of claim 2, wherein said membrane bound Fas ligand mutein has an amino acid sequence that is the same as the amino acid sequence in SEQ ID NO: 6 or SEQ ID NO: 10.

4. The Fas ligand agonist of claim 3, wherein said membrane bound Fas ligand mutein has an amino acid sequence that is the same as the amino acid sequence in SEQ ID NO: 6.

5. The Fas ligand agonist of claim 3, wherein said membrane bound Fas ligand mutein has an amino acid sequence that is the same as the amino acid sequence in SEQ ID NO: 10.

6. The Fas ligand agonist of claim 1, wherein said Fas ligand chimera is membrane bound.

7. The Fas ligand agonist of claim 6, wherein said Fas ligand chimera has an amino acid sequence that corresponds to the fusion product of the carboxy terminus of the transmembrane domain of CD30 ligand fused to the amino terminus of the extracellular domain of Fas ligand, said extracellular domain lacking a continuous segment of 10 to 17 amino acid residues beginning at about residue position 130 of pro-Fas ligand.

8. The Fas ligand agonist of claim 7, wherein said Fas ligand chimera has an amino acid sequence corresponding to the fusion product of the carboxy terminus of residues 1–86 of CD30 ligand fused to the amino terminus of the extracellular domain of Fas ligand, said extracellular domain beginning 10 to 17 amino acid residues beyond about residue position 130 and extending to residue position 281 of pro-Fas.

9. The Fas ligand agonist of claim 6, wherein said Fas ligand chimera has an amino acid sequence corresponding to the fusion product of the carboxy terminus of the transmembrane domain of CD40 ligand fused to the amino terminus of the extracellular domain of Fas ligand, said extracellular domain lacking a continuous segment of 10 to 17 amino acid residues beginning at about residue position 130 of pro-Fas ligand.

10. The Fas ligand agonist of claim 9, wherein said Fas ligand chimera has an amino acid sequence corresponding to the fusion product of the carboxy terminus of residues 1–107 of CD40 ligand fused to the amino terminus of the extracellular domain of Fas ligand, said extracellular domain beginning 10 to 17 amino acid residues beyond about residue position 130 and extending to residue position 281 of pro-Fas ligand.

11. The Fas ligand agonist of claim 1, wherein said Fas ligand deletion mutein or said Fas ligand chimera is bound to the membrane of a host cell.

12. The Fas ligand agonist of claim 11, wherein said host cell is a human host cell.

13. A DNA consisting essentially of SEQ ID NO: 5 or SEQ ID NO: 7.

14. A DNA encoding a Pas ligand agonist of SEQ ID NO: 6 or SEQ ID NO: 8.

15. A transformed human host cell, said host cell expressing recombinant Fas ligand agonist that is membrane bound thereto and substantially non-cleavable therefrom by proteinases or convertases, said Fas ligand agonist binding to Fas.

16. The transformed human host cell of claim 15, wherein said recombinant Fas ligand agonist is a Fas ligand deletion mutein lacking a continuous segment of 10 to 17 amino acid residues beginning at about residue position 130 of pro-Fas ligand.

17. A vector comprising a promoter operably linked to a recombinant gene encoding a Fas ligand deletion mutein or a Fas ligand chimera, said Fas ligand deletion mutein comprising the transmembrane region of Fas ligand said transmembrane region being residue 1 up to residue 129 of SEQ ID NO: 12 linked by a peptide linkage that is substantially non-cleavable from a cell membrane by proteinases or convertases to the Fas-binding domain of human Fas ligand beginning from about residue 139 to residue 146 of SEQ ID NO: 12, said Fas ligand chimera comprising the transmembrane region of a cell surface protein linked by a peptide linkage that is substantially non-cleavable from a cell membrane by proteinases or convertases to the Fas-binding domain of human Fas ligand beginning from about residue 139 to residue 146 of SEQ ID NO: 12.

18. The vector of claim 17, wherein said vector is selected from the group consisting of a retroviral vector, an adenoviral vector, and an adenoassociated viral vector.

19. The vector of claim 17, wherein said recombinant gene encodes said Fas ligant deletion mutein.

20. The vector of claim 19, wherein said Fas ligand deletion mutein has a 130→142 deletion.

21. The vector of claim 19, wherein said Fas ligand deletion mutein has a 130→145 deletion.

22. The vector of claim 17, wherein said Fas ligand chimera has a transmembrane domain that is selected from a member of the tumor necrosis factor receptor superfamily.

23. The vector of claim 22, wherein said transmembrane domain is selected from a member of the group consisting of tumor necrosis factor receptor, CD30, nerve growth factor receptor, CD27, CD40, CD120a, CD120b, lymphotoxin beta receptor and TRAIL receptor.

24. A DNA consisting essentially of SEQ ID NO: 9.

25. A DNA encoding a Fas ligand agonist of SEQ ID NO: 10.

26. A Fas ligand agonist being a Fas ligand chimera comprising a Fas ligand of SEQ ID NO: 12, wherein a continuous segment of 10 to 17 amino acid residues beginning at about residue position 130 has been replaced by a continuous segment of amino acid residues that are substantially non-cleavable from a cell membrane by proteinases or convertases.

27. The Fas ligand agonist of claim 26, wherein said continuous segment of amino acid residues that are substantially non-cleavable from a cell membrane by proteinases or convertases is a transmembrane domain of a cell surface protein other than Fas ligand.

* * * * *

SEQUENCE LISTING

```
(1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 387 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 1..387

(xi) SEQUENCE DESCRIPTION: SEQ ID NO:1:

ATG CAG CAG CCC TTC AAT TAC CCA TAT CCC CAG ATC TAC TGG GTG GAC       48
Met Gln Gln Pro Phe Asn Tyr Pro Tyr Pro Gln Ile Tyr Trp Val Asp
  1               5                  10                  15

AGC AGT GCC AGC TCT CCC TGG GCC CCT CCA GGC ACA GTT CTT CCC TGT       96
Ser Ser Ala Ser Ser Pro Trp Ala Pro Pro Gly Thr Val Leu Pro Cys
             20                  25                  30

CCA ACC TCT GTG CCC AGA AGG CCT GGT CAA AGG AGG CCA CCA CCA CCA      144
Pro Thr Ser Val Pro Arg Arg Pro Gly Gln Arg Arg Pro Pro Pro Pro
         35                  40                  45

CCG CCA CCG CCA CCA CTA CCA CCT CCG CCG CCG CCG CCA CCA CTG CCT      192
Pro Pro Pro Pro Pro Leu Pro Pro Pro Pro Pro Pro Pro Pro Leu Pro
     50                  55                  60

CCA CTA CCG CTG CCA CCC CTG AAG AAG AGA GGG AAC CAC AGC ACA GGC      240
Pro Leu Pro Leu Pro Pro Leu Lys Lys Arg Gly Asn His Ser Thr Gly
 65                  70                  75                  80

CTG TGT CTC CTT GTG ATG TTT TTC ATG GTT CTG GTT GCC TTG GTA GGA      288
Leu Cys Leu Leu Val Met Phe Phe Met Val Leu Val Ala Leu Val Gly
                 85                  90                  95

TTG GGC CTG GGG ATG TTT CAG CTC TTC CAC CTA CAG AAG GAG CTG GCA      336
Leu Gly Leu Gly Met Phe Gln Leu Phe His Leu Gln Lys Glu Leu Ala
            100                 105                 110
```

```
GAA CTC CGA GAG TCT ACC AGC CAG ATG CAC ACA GCA TCA TCT TTG GAG        384
Glu Leu Arg Glu Ser Thr Ser Gln Met His Thr Ala Ser Ser Leu Glu
        115                 120                 125

AAG                                                                    387
Lys
```

(2) INFORMATION FOR SEQ ID NO:2:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Pro Pro Pro Pro
        35                  40                  45

Pro Pro Pro Pro Pro Leu Pro Pro Pro Pro Pro Pro Leu Pro
    50                  55                  60

Pro Leu Pro Leu Pro Pro Leu Lys Lys Arg Gly Asn His Ser Thr Gly
 65                 70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys
```

(2) INFORMATION FOR SEQ ID NO:3:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..420

(xi) SEQUENCE DESCRIPTION: SEQ ID NO:3:

```
CTG AGG AAA GTG GCC CAT TTA ACA GGC AAG TCC AAC TCA AGG TCC ATG        48
Leu Arg Lys Val Ala His Leu Thr Gly Lys Ser Asn Ser Arg Ser Met
 1               5                  10                  15

CCT CTG GAA TGG GAA GAC ACC TAT GGA ATT GTC CTG CTT TCT GGA GTG        96
Pro Leu Glu Trp Glu Asp Thr Tyr Gly Ile Val Leu Leu Ser Gly Val
            20                  25                  30

AAG TAT AAG AAG GGT GGC CTT GTG ATC AAT GAA ACT GGG CTG TAC TTT       144
Lys Tyr Lys Lys Gly Gly Leu Val Ile Asn Glu Thr Gly Leu Tyr Phe
        35                  40                  45

GTA TAT TCC AAA GTA TAC TTC CGG GGT CAA TCT TGC AAC AAC CTG CCC       192
Val Tyr Ser Lys Val Tyr Phe Arg Gly Gln Ser Cys Asn Asn Leu Pro
    50                  55                  60
```

```
CTG AGC CAC AAG GTC TAC ATG AGG AAC TCT AAG TAT CCC CAG GAT CTG        240
Leu Ser His Lys Val Tyr Met Arg Asn Ser Lys Tyr Pro Gln Asp Leu
65                  70                  75                  80

GTG ATG ATG GAG GGG AAG ATG ATG AGC TAC TGC ACT ACT GGG CAG ATG        288
Val Met Met Glu Gly Lys Met Met Ser Tyr Cys Thr Thr Gly Gln Met
                85                  90                  95

TGG GCC CGC AGC AGC TAC CTG GGG GCA GTG TTC AAT CTT ACC AGT GCT        336
Trp Ala Arg Ser Ser Tyr Leu Gly Ala Val Phe Asn Leu Thr Ser Ala
            100                 105                 110

GAT CAT TTA TAT GTC AAC GTA TCT GAG CTC TCT CTG GTC AAT TTT GAG        384
Asp His Leu Tyr Val Asn Val Ser Glu Leu Ser Leu Val Asn Phe Glu
        115                 120                 125

GAA TCT CAG ACG TTT TTC GGC TTA TAT AAG CTC TAA                        420
Glu Ser Gln Thr Phe Phe Gly Leu Tyr Lys Leu
130                 135                 140
```

(2) INFORMATION FOR SEQ ID NO:4:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:4:

```
Leu Arg Lys Val Ala His Leu Thr Gly Lys Ser Asn Ser Arg Ser Met
1               5                   10                  15

Pro Leu Glu Trp Glu Asp Thr Tyr Gly Ile Val Leu Leu Ser Gly Val
                20                  25                  30

Lys Tyr Lys Lys Gly Gly Leu Val Ile Asn Glu Thr Gly Leu Tyr Phe
            35                  40                  45

Val Tyr Ser Lys Val Tyr Phe Arg Gly Gln Ser Cys Asn Asn Leu Pro
        50                  55                  60

Leu Ser His Lys Val Tyr Met Arg Asn Ser Lys Tyr Pro Gln Asp Leu
65                  70                  75                  80

Val Met Met Glu Gly Lys Met Met Ser Tyr Cys Thr Thr Gly Gln Met
                85                  90                  95

Trp Ala Arg Ser Ser Tyr Leu Gly Ala Val Phe Asn Leu Thr Ser Ala
            100                 105                 110

Asp His Leu Tyr Val Asn Val Ser Glu Leu Ser Leu Val Asn Phe Glu
        115                 120                 125

Glu Ser Gln Thr Phe Phe Gly Leu Tyr Lys Leu
130                 135
```

(2) INFORMATION FOR SEQ ID NO:5:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..807

(xi) SEQUENCE DESCRIPTION: SEQ ID NO:5:

```
ATG CAG CAG CCC TTC AAT TAC CCA TAT CCC CAG ATC TAC TGG GTG GAC         48
Met Gln Gln Pro Phe Asn Tyr Pro Tyr Pro Gln Ile Tyr Trp Val Asp
1               5                   10                  15
```

```
AGC AGT GCC AGC TCT CCC TGG GCC CCT CCA GGC ACA GTT CTT CCC TGT        96
Ser Ser Ala Ser Ser Pro Trp Ala Pro Pro Gly Thr Val Leu Pro Cys
            20                  25                  30

CCA ACC TCT GTG CCC AGA AGG CCT GGT CAA AGG AGG CCA CCA CCA CCA       144
Pro Thr Ser Val Pro Arg Arg Pro Gly Gln Arg Arg Pro Pro Pro Pro
                35                  40                  45

CCG CCA CCG CCA CCA CTA CCA CCT CCG CCG CCG CCA CCA CTG CCT           192
Pro Pro Pro Pro Pro Leu Pro Pro Pro Pro Pro Pro Pro Leu Pro
        50                  55                  60

CCA CTA CCG CTG CCA CCC CTG AAG AAG AGA GGG AAC CAC AGC ACA GGC       240
Pro Leu Pro Leu Pro Pro Leu Lys Lys Arg Gly Asn His Ser Thr Gly
65                  70                  75                  80

CTG TGT CTC CTT GTG ATG TTT TTC ATG GTT CTG GTT GCC TTG GTA GGA       288
Leu Cys Leu Leu Val Met Phe Phe Met Val Leu Val Ala Leu Val Gly
                85                  90                  95

TTG GGC CTG GGG ATG TTT CAG CTC TTC CAC CTA CAG AAG GAG CTG GCA       336
Leu Gly Leu Gly Met Phe Gln Leu Phe His Leu Gln Lys Glu Leu Ala
            100                 105                 110

GAA CTC CGA GAG TCT ACC AGC CAG ATG CAC ACA GCA TCA TCT TTG GAG       384
Glu Leu Arg Glu Ser Thr Ser Gln Met His Thr Ala Ser Ser Leu Glu
            115                 120                 125

AAG CTG AGG AAA GTG GCC CAT TTA ACA GGC AAG TCC AAC TCA AGG TCC       432
Lys Leu Arg Lys Val Ala His Leu Thr Gly Lys Ser Asn Ser Arg Ser
130                 135                 140

ATG CCT CTG GAA TGG GAA GAC ACC TAT GGA ATT GTC CTG CTT TCT GGA       480
Met Pro Leu Glu Trp Glu Asp Thr Tyr Gly Ile Val Leu Leu Ser Gly
145                 150                 155                 160

GTG AAG TAT AAG AAG GGT GGC CTT GTG ATC AAT GAA ACT GGG CTG TAC       528
Val Lys Tyr Lys Lys Gly Gly Leu Val Ile Asn Glu Thr Gly Leu Tyr
                165                 170                 175

TTT GTA TAT TCC AAA GTA TAC TTC CGG GGT CAA TCT TGC AAC AAC CTG       576
Phe Val Tyr Ser Lys Val Tyr Phe Arg Gly Gln Ser Cys Asn Asn Leu
            180                 185                 190

CCC CTG AGC CAC AAG GTC TAC ATG AGG AAC TCT AAG TAT CCC CAG GAT       624
Pro Leu Ser His Lys Val Tyr Met Arg Asn Ser Lys Tyr Pro Gln Asp
            195                 200                 205

CTG GTG ATG ATG GAG GGG AAG ATG ATG AGC TAC TGC ACT ACT GGG CAG       672
Leu Val Met Met Glu Gly Lys Met Met Ser Tyr Cys Thr Thr Gly Gln
            210                 215                 220

ATG TGG GCC CGC AGC AGC TAC CTG GGG GCA GTG TTC AAT CTT ACC AGT       720
Met Trp Ala Arg Ser Ser Tyr Leu Gly Ala Val Phe Asn Leu Thr Ser
225                 230                 235                 240

GCT GAT CAT TTA TAT GTC AAC GTA TCT GAG CTC TCT CTG GTC AAT TTT       768
Ala Asp His Leu Tyr Val Asn Val Ser Glu Leu Ser Leu Val Asn Phe
                245                 250                 255

GAG GAA TCT CAG ACG TTT TTC GGC TTA TAT AAG CTC TAA                   807
Glu Glu Ser Gln Thr Phe Phe Gly Leu Tyr Lys Leu
            260                 265
```

(2) INFORMATION FOR SEQ ID NO:6:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gln Gln Pro Phe Asn Tyr Pro Tyr Pro Gln Ile Tyr Trp Val Asp
  1               5                  10                  15
```

```
Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
        35                  40                  45

Pro Pro Pro Pro Pro Leu Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Leu Arg Lys Val Ala His Leu Thr Gly Lys Ser Asn Ser Arg Ser
        130                 135                 140

Met Pro Leu Glu Trp Glu Asp Thr Tyr Gly Ile Val Leu Leu Ser Gly
145                 150                 155                 160

Val Lys Tyr Lys Lys Gly Gly Leu Val Ile Asn Glu Thr Gly Leu Tyr
                165                 170                 175

Phe Val Tyr Ser Lys Val Tyr Phe Arg Gly Gln Ser Cys Asn Asn Leu
            180                 185                 190

Pro Leu Ser His Lys Val Tyr Met Arg Asn Ser Lys Tyr Pro Gln Asp
        195                 200                 205

Leu Val Met Met Glu Gly Lys Met Met Ser Tyr Cys Thr Thr Gly Gln
    210                 215                 220

Met Trp Ala Arg Ser Ser Tyr Leu Gly Ala Val Phe Asn Leu Thr Ser
225                 230                 235                 240

Ala Asp His Leu Tyr Val Asn Val Ser Glu Leu Ser Leu Val Asn Phe
                245                 250                 255

Glu Glu Ser Gln Thr Phe Phe Gly Leu Tyr Lys Leu
            260                 265
```

(2) INFORMATION FOR SEQ ID NO:7:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..411

(xi) SEQUENCE DESCRIPTION: SEQ ID NO:7:

```
GTG GCC CAT TTA ACA GGC AAG TCC AAC TCA AGG TCC ATG CCT CTG GAA      48
Val Ala His Leu Thr Gly Lys Ser Asn Ser Arg Ser Met Pro Leu Glu
  1               5                  10                  15

TGG GAA GAC ACC TAT GGA ATT GTC CTG CTT TCT GGA GTG AAG TAT AAG      96
Trp Glu Asp Thr Tyr Gly Ile Val Leu Leu Ser Gly Val Lys Tyr Lys
                20                  25                  30

AAG GGT GGC CTT GTG ATC AAT GAA ACT GGG CTG TAC TTT GTA TAT TCC     144
Lys Gly Gly Leu Val Ile Asn Glu Thr Gly Leu Tyr Phe Val Tyr Ser
            35                  40                  45

AAA GTA TAC TTC CGG GGT CAA TCT TGC AAC AAC CTG CCC CTG AGC CAC     192
```

```
AAG GTC TAC ATG AGG AAC TCT AAG TAT CCC CAG GAT CTG GTG ATG ATG        240
Lys Val Tyr Met Arg Asn Ser Lys Tyr Pro Gln Asp Leu Val Met Met
 65                  70                  75                  80

GAG GGG AAG ATG ATG AGC TAC TGC ACT ACT GGG CAG ATG TGG GCC CGC        288
Glu Gly Lys Met Met Ser Tyr Cys Thr Thr Gly Gln Met Trp Ala Arg
                 85                  90                  95

AGC AGC TAC CTG GGG GCA GTG TTC AAT CTT ACC AGT GCT GAT CAT TTA        336
Ser Ser Tyr Leu Gly Ala Val Phe Asn Leu Thr Ser Ala Asp His Leu
            100                 105                 110

TAT GTC AAC GTA TCT GAG CTC TCT CTG GTC AAT TTT GAG GAA TCT CAG        384
Tyr Val Asn Val Ser Glu Leu Ser Leu Val Asn Phe Glu Glu Ser Gln
        115                 120                 125

ACG TTT TTC GGC TTA TAT AAG CTC TAA                                    411
Thr Phe Phe Gly Leu Tyr Lys Leu
    130                 135
```

(2) INFORMATION FOR SEQ ID NO:8:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:8:

```
Val Ala His Leu Thr Gly Lys Ser Asn Ser Arg Ser Met Pro Leu Glu
  1               5                  10                  15

Trp Glu Asp Thr Tyr Gly Ile Val Leu Leu Ser Gly Val Lys Tyr Lys
                 20                  25                  30

Lys Gly Gly Leu Val Ile Asn Glu Thr Gly Leu Tyr Phe Val Tyr Ser
             35                  40                  45

Lys Val Tyr Phe Arg Gly Gln Ser Cys Asn Asn Leu Pro Leu Ser His
         50                  55                  60

Lys Val Tyr Met Arg Asn Ser Lys Tyr Pro Gln Asp Leu Val Met Met
 65                  70                  75                  80

Glu Gly Lys Met Met Ser Tyr Cys Thr Thr Gly Gln Met Trp Ala Arg
                 85                  90                  95

Ser Ser Tyr Leu Gly Ala Val Phe Asn Leu Thr Ser Ala Asp His Leu
            100                 105                 110

Tyr Val Asn Val Ser Glu Leu Ser Leu Val Asn Phe Glu Glu Ser Gln
        115                 120                 125

Thr Phe Phe Gly Leu Tyr Lys Leu
    130                 135
```

(2) INFORMATION FOR SEQ ID NO:9:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..798

(xi) SEQUENCE DESCRIPTION: SEQ ID NO:9:

```
ATG CAG CAG CCC TTC AAT TAC CCA TAT CCC CAG ATC TAC TGG GTG GAC        48
Met Gln Gln Pro Phe Asn Tyr Pro Tyr Pro Gln Ile Tyr Trp Val Asp
 1               5                  10                  15

AGC AGT GCC AGC TCT CCC TGG GCC CCT CCA GGC ACA GTT CTT CCC TGT        96
Ser Ser Ala Ser Ser Pro Trp Ala Pro Pro Gly Thr Val Leu Pro Cys
             20                  25                  30

CCA ACC TCT GTG CCC AGA AGG CCT GGT CAA AGG AGG CCA CCA CCA CCA       144
Pro Thr Ser Val Pro Arg Arg Pro Gly Gln Arg Arg Pro Pro Pro Pro
         35                  40                  45

CCG CCA CCG CCA CCA CTA CCA CCT CCG CCG CCG CCG CCA CCA CTG CCT       192
Pro Pro Pro Pro Pro Leu Pro Pro Pro Pro Pro Pro Pro Pro Leu Pro
     50                  55                  60

CCA CTA CCG CTG CCA CCC CTG AAG AAG AGA GGG AAC CAC AGC ACA GGC       240
Pro Leu Pro Leu Pro Pro Leu Lys Lys Arg Gly Asn His Ser Thr Gly
 65                  70                  75                  80

CTG TGT CTC CTT GTG ATG TTT TTC ATG GTT CTG GTT GCC TTG GTA GGA       288
Leu Cys Leu Leu Val Met Phe Phe Met Val Leu Val Ala Leu Val Gly
                 85                  90                  95

TTG GGC CTG GGG ATG TTT CAG CTC TTC CAC CTA CAG AAG GAG CTG GCA       336
Leu Gly Leu Gly Met Phe Gln Leu Phe His Leu Gln Lys Glu Leu Ala
             100                 105                 110

GAA CTC CGA GAG TCT ACC AGC CAG ATG CAC ACA GCA TCA TCT TTG GAG       384
Glu Leu Arg Glu Ser Thr Ser Gln Met His Thr Ala Ser Ser Leu Glu
         115                 120                 125

AAG GTG GCC CAT TTA ACA GGC AAG TCC AAC TCA AGG TCC ATG CCT CTG       432
Lys Val Ala His Leu Thr Gly Lys Ser Asn Ser Arg Ser Met Pro Leu
     130                 135                 140

GAA TGG GAA GAC ACC TAT GGA ATT GTC CTG CTT TCT GGA GTG AAG TAT       480
Glu Trp Glu Asp Thr Tyr Gly Ile Val Leu Leu Ser Gly Val Lys Tyr
145                 150                 155                 160

AAG AAG GGT GGC CTT GTG ATC AAT GAA ACT GGG CTG TAC TTT GTA TAT       528
Lys Lys Gly Gly Leu Val Ile Asn Glu Thr Gly Leu Tyr Phe Val Tyr
                 165                 170                 175

TCC AAA GTA TAC TTC CGG GGT CAA TCT TGC AAC AAC CTG CCC CTG AGC       576
Ser Lys Val Tyr Phe Arg Gly Gln Ser Cys Asn Asn Leu Pro Leu Ser
             180                 185                 190

CAC AAG GTC TAC ATG AGG AAC TCT AAG TAT CCC CAG GAT CTG GTG ATG       624
His Lys Val Tyr Met Arg Asn Ser Lys Tyr Pro Gln Asp Leu Val Met
         195                 200                 205

ATG GAG GGG AAG ATG ATG AGC TAC TGC ACT ACT GGG CAG ATG TGG GCC       672
Met Glu Gly Lys Met Met Ser Tyr Cys Thr Thr Gly Gln Met Trp Ala
     210                 215                 220

CGC AGC AGC TAC CTG GGG GCA GTG TTC AAT CTT ACC AGT GCT GAT CAT       720
Arg Ser Ser Tyr Leu Gly Ala Val Phe Asn Leu Thr Ser Ala Asp His
225                 230                 235                 240

TTA TAT GTC AAC GTA TCT GAG CTC TCT CTG GTC AAT TTT GAG GAA TCT       768
Leu Tyr Val Asn Val Ser Glu Leu Ser Leu Val Asn Phe Glu Glu Ser
                 245                 250                 255

CAG ACG TTT TTC GGC TTA TAT AAG CTC TAA                              798
Gln Thr Phe Phe Gly Leu Tyr Lys Leu
             260                 265
```

(2) INFORMATION FOR SEQ ID NO:10:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Val Ala His Leu Thr Gly Lys Ser Asn Ser Arg Ser Met Pro Leu
130                 135                 140

Glu Trp Glu Asp Thr Tyr Gly Ile Val Leu Leu Ser Gly Val Lys Tyr
145                 150                 155                 160

Lys Lys Gly Gly Leu Val Ile Asn Glu Thr Gly Leu Tyr Phe Val Tyr
                165                 170                 175

Ser Lys Val Tyr Phe Arg Gly Gln Ser Cys Asn Asn Leu Pro Leu Ser
                180                 185                 190

His Lys Val Tyr Met Arg Asn Ser Lys Tyr Pro Gln Asp Leu Val Met
            195                 200                 205

Met Glu Gly Lys Met Met Ser Tyr Cys Thr Thr Gly Gln Met Trp Ala
210                 215                 220

Arg Ser Ser Tyr Leu Gly Ala Val Phe Asn Leu Thr Ser Ala Asp His
225                 230                 235                 240

Leu Tyr Val Asn Val Ser Glu Leu Ser Leu Val Asn Phe Glu Glu Ser
                245                 250                 255

Gln Thr Phe Phe Gly Leu Tyr Lys Leu
            260                 265

(2) INFORMATION FOR SEQ ID NO:11:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 65..910

(xi) SEQUENCE DESCRIPTION: SEQ ID NO:11:

TCTAGACTCA GGACTGAGAA GAAGTAAAAC CGTTTGCTGG GGCTGGCCTG ACTCACCAGC      60

TGCC ATG CAG CAG CCC TTC AAT TAC CCA TAT CCC CAG ATC TAC TGG GTG     109
     Met Gln Gln Pro Phe Asn Tyr Pro Tyr Pro Gln Ile Tyr Trp Val
      1               5                  10                  15

GAC AGC AGT GCC AGC TCT CCC TGG GCC CCT CCA GGC ACA GTT CTT CCC     157
Asp Ser Ser Ala Ser Ser Pro Trp Ala Pro Pro Gly Thr Val Leu Pro
                 20                  25                  30
```

```
TGT CCA ACC TCT GTG CCC AGA AGG CCT GGT CAA AGG AGG CCA CCA CCA       205
Cys Pro Thr Ser Val Pro Arg Arg Pro Gly Gln Arg Arg Pro Pro Pro
            35                  40                  45

CCA CCG CCA CCA CCA CTA CCA CCT CCG CCG CCG CCA CCA CTG               253
Pro Pro Pro Pro Pro Leu Pro Pro Pro Pro Pro Pro Pro Leu
        50                  55                  60

CCT CCA CTA CCG CTG CCA CCC CTG AAG AAG AGA GGG AAC CAC AGC ACA       301
Pro Pro Leu Pro Leu Pro Pro Leu Lys Lys Arg Gly Asn His Ser Thr
            65                  70                  75

GGC CTG TGT CTC CTT GTG ATG TTT TTC ATG GTT CTG GTT GCC TTG GTA       349
Gly Leu Cys Leu Leu Val Met Phe Phe Met Val Leu Val Ala Leu Val
 80                  85                  90                  95

GGA TTG GGC CTG GGG ATG TTT CAG CTC TTC CAC CTA CAG AAG GAG CTG       397
Gly Leu Gly Leu Gly Met Phe Gln Leu Phe His Leu Gln Lys Glu Leu
                100                 105                 110

GCA GAA CTC CGA GAG TCT ACC AGC CAG ATG CAC ACA GCA TCA TCT TTG       445
Ala Glu Leu Arg Glu Ser Thr Ser Gln Met His Thr Ala Ser Ser Leu
            115                 120                 125

GAG AAG CAA ATA GGC CAC CCC AGT CCA CCC CCT GAA AAA AAG GAG CTG       493
Glu Lys Gln Ile Gly His Pro Ser Pro Pro Pro Glu Lys Lys Glu Leu
        130                 135                 140

AGG AAA GTG GCC CAT TTA ACA GGC AAG TCC AAC TCA AGG TCC ATG CCT       541
Arg Lys Val Ala His Leu Thr Gly Lys Ser Asn Ser Arg Ser Met Pro
145                 150                 155

CTG GAA TGG GAA GAC ACC TAT GGA ATT GTC CTG CTT TCT GGA GTG AAG       589
Leu Glu Trp Glu Asp Thr Tyr Gly Ile Val Leu Leu Ser Gly Val Lys
160                 165                 170                 175

TAT AAG AAG GGT GGC CTT GTG ATC AAT GAA ACT GGG CTG TAC TTT GTA       637
Tyr Lys Lys Gly Gly Leu Val Ile Asn Glu Thr Gly Leu Tyr Phe Val
                180                 185                 190

TAT TCC AAA GTA TAC TTC CGG GGT CAA TCT TGC AAC AAC CTG CCC CTG       685
Tyr Ser Lys Val Tyr Phe Arg Gly Gln Ser Cys Asn Asn Leu Pro Leu
            195                 200                 205

AGC CAC AAG GTC TAC ATG AGG AAC TCT AAG TAT CCC CAG GAT CTG GTG       733
Ser His Lys Val Tyr Met Arg Asn Ser Lys Tyr Pro Gln Asp Leu Val
        210                 215                 220

ATG ATG GAG GGG AAG ATG ATG AGC TAC TGC ACT ACT GGG CAG ATG TGG       781
Met Met Glu Gly Lys Met Met Ser Tyr Cys Thr Thr Gly Gln Met Trp
225                 230                 235

GCC CGC AGC AGC TAC CTG GGG GCA GTG TTC AAT CTT ACC AGT GCT GAT       829
Ala Arg Ser Ser Tyr Leu Gly Ala Val Phe Asn Leu Thr Ser Ala Asp
240                 245                 250                 255

CAT TTA TAT GTC AAC GTA TCT GAG CTC TCT CTG GTC AAT TTT GAG GAA       877
His Leu Tyr Val Asn Val Ser Glu Leu Ser Leu Val Asn Phe Glu Glu
                260                 265                 270

TCT CAG ACG TTT TTC GGC TTA TAT AAG CTC TAAGAGAAGC ACTTTGGGAT        927
Ser Gln Thr Phe Phe Gly Leu Tyr Lys Leu
            275                 280

TCTTTCCATT ATGATTCTTT GTTACAGGCA CCGAGATGTT CTAGA                    972

(2) INFORMATION FOR SEQ ID NO:12:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:12:

Met Gln Gln Pro Phe Asn Tyr Pro Tyr Pro Gln Ile Tyr Trp Val Asp
```

-continued

```
  1               5                    10                   15
Ser Ser Ala Ser Ser Pro Trp Ala Pro Pro Gly Thr Val Leu Pro Cys
            20                  25                  30
Pro Thr Ser Val Pro Arg Arg Pro Gly Gln Arg Arg Pro Pro Pro Pro
            35                  40                  45
Pro Pro Pro Pro Pro Leu Pro Pro Pro Pro Pro Pro Pro Leu Pro
    50                  55                  60
Pro Leu Pro Leu Pro Leu Lys Lys Arg Gly Asn His Ser Thr Gly
 65                 70                  75                  80
Leu Cys Leu Leu Val Met Phe Phe Met Val Leu Val Ala Leu Val Gly
                85                  90                  95
Leu Gly Leu Gly Met Phe Gln Leu Phe His Leu Gln Lys Glu Leu Ala
                100                 105                 110
Glu Leu Arg Glu Ser Thr Ser Gln Met His Thr Ala Ser Ser Leu Glu
            115                 120                 125
Lys Gln Ile Gly His Pro Ser Pro Pro Pro Glu Lys Lys Glu Leu Arg
 130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
                180                 185                 190
Ser Lys Val Tyr Phe Arg Gly Gln Ser Cys Asn Asn Leu Pro Leu Ser
            195                 200                 205
His Lys Val Tyr Met Arg Asn Ser Lys Tyr Pro Gln Asp Leu Val Met
            210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
                260                 265                 270
Gln Thr Phe Phe Gly Leu Tyr Lys Leu
            275                 280
```